US008436140B2

(12) United States Patent  
Woodard et al.

(10) Patent No.: US 8,436,140 B2  
(45) Date of Patent: May 7, 2013

(54) NATRIURETIC PEPTIDE-MEDIATED IMAGING OF ATHEROSCLEROTIC PLAQUE

(75) Inventors: Pamela K. Woodard, St. Louis, MO (US); Michael J. Welch, Clayton, MO (US); Geoffrey E. Woodard, Newton, MA (US); Rafaella Rossin, Eindhoven (NL)

(73) Assignee: Washington University, Saint Louis, MO (US)

( * ) Notice: Subject to any disclaimer, the term of this patent is extended or adjusted under 35 U.S.C. 154(b) by 670 days.

(21) Appl. No.: 12/454,810

(22) Filed: May 22, 2009

(65) Prior Publication Data

US 2010/0021381 A1    Jan. 28, 2010

Related U.S. Application Data

(60) Provisional application No. 61/130,681, filed on Jun. 2, 2008.

(51) Int. Cl.
*C07K 9/00*    (2006.01)

(52) U.S. Cl.
USPC .......... 530/327; 530/326; 514/12.4; 424/1.69

(58) Field of Classification Search .................. 530/327, 530/326; 514/12.4; 424/1.69
See application file for complete search history.

(56) References Cited

U.S. PATENT DOCUMENTS

| | | | | |
|---|---|---|---|---|
| 4,716,147 | A * | 12/1987 | Tjoeng et al. | 514/11.3 |
| 4,721,704 | A * | 1/1988 | Chang et al. | 514/9.7 |
| 4,764,504 | A * | 8/1988 | Johnson et al. | 514/15.4 |
| 5,212,286 | A * | 5/1993 | Lewicki et al. | 530/324 |
| 5,565,606 | A * | 10/1996 | Breiphol et al. | 560/158 |
| 5,679,777 | A * | 10/1997 | Anderson et al. | 530/385 |
| 7,556,795 | B2 * | 7/2009 | Chen et al. | 424/1.69 |
| 2003/0121063 | A1 * | 6/2003 | Kazazian et al. | 800/8 |
| 2000/0026673 | * | 12/2004 | Bakis | 514/12 |
| 2008/0207522 | A1 * | 8/2008 | Hancock et al. | 514/14 |
| 2009/0175821 | A1 * | 7/2009 | Bridon et al. | 424/85.5 |

OTHER PUBLICATIONS

Inagami (J Biol Chem 264, 3043-46, 1989).*
Scarborough, R.M. (Journal of Biological Chemistry 261(28):12960-12964, 1986).*
Ahluwalia et al, Endothelium-derived C-type natriuretic peptide: more than just a hyperpolarizing factor. Trends Pharmacol Sci, 2005, 26(3):162-167.
Apple et al, Future biomarkers for detection of ischemia and risk stratification in acute coronary syndrome, Clin Chem, 2005, 51:810-824.
Collinson et al, Biomarkers of Cardiovascular Damage and Dysfunction—An overview, Heart Lung and Circulation, 2007, 16:S71-S82.
Collinson et al, Biomarkers of cardiovascular damage, Med Principles and Practice, 2007, 16:247-261.
Daniels et al, Natriuretic peptides, J Am Coll Cardiol, 2007, 50(25):2357-2368.
Davies et al, Molecular and metabolic imaging of atherosclerosis, J Nucl Med, 2004, 45(11):1898-1907.
Fayad et al, Clinical imaging of the high-risk or vulnerable atherosclerotic plaque, Circ Res, 2001, 89(4):305-316.
Fayad, Noncoronary and coronary atherothrombotic plaque imaging and monitoring of therapy by MRI, Neuroimaging Clin N Am, 2002, 12(3):461-471.
Hardoff et al, External imaging of atherosclerosis in rabbits using an 123I-labeled synthetic peptide fragment, J Clin Pharmacol, 1993, 33(11):1039-104.
Hobbs et al, Natriuretic peptide receptor-C regulates coronary blood flow and prevents myocardial ischemia/reperfusion injury: novel cardioprotective role for endothelium-derived C-type natriuretic peptide, Circulation, 2004, 110 (10):1231-1235.
Jaffer et al, Molecular and cellular imaging of atherosclerosis: emerging applications. J Am Coll Cardiol, 2006, 47 (7):1328-1338.
Kalra et al, The role of C-type natriuretic peptide in cardiovascular medicine, Eur Heart J, 2001, 12(12):997-1007.
Lambert et al, Receptor imaging with atrial natriuretic peptide. Part 1: High specific activity iodine-123-atrial natriuretic peptide, J Nucl Med, 1994, 35:628-637.
Langer et al, Radionuclide imaging: a molecular key to the atherosclerotic plaque. J Am Coll Cardiol, 2008, 52 (1):1-12.
Laurberg et al, Imaging of vulnerable atherosclerotic plaques with FDG-microPET: no FDG accumulation, Atherosclerosis, 2007, 192(2):275-282.
Lerakis et al, Imaging of the vulnerable plaque: noninvasive and invasive techniques, Am J Med Sci, 2008, 336 (4):342-348.
Meding et al, Magnetic resonance imaging of atherosclerosis by targeting extracellular matrix deposition with Gadofluorine M. Contrast Media Mol Imaging, 2007, 2(3):120-129.
Naruko et al, C-type natriuretic peptide in human coronary atherosclerotic lesions, Circulation, 1996, 94 (12):3103-3108.
Ogawa et al, (18)F-FDG accumulation in atherosclerotic plaques: immunohistochemical and PET imaging study, J Nucl Med, 2004, 45(7):1245-1250.
Rossin et al, In vivo imaging of 64Cu-labeled polymer nanoparticles targeted to the lung endothelium, J Nucl Med, 2008, 49(1):103-111.
Rudd et al, Atherosclerosis inflammation imaging with 18F-FDG PET: carotid, iliac, and femoral uptake reproducibility, quantification methods, and recommendations, J Nucl Med, 2008, 49(6):871-878.
Rudd et al, Imaging atherosclerotic plaque inflammation with [18F]-fluorodeoxyglucose positron emission tomography, Circulation, 2002, 105(23):2708-2711.
Saam et al, The vulnerable, or high-risk, atherosclerotic plaque: noninvasive MR imaging for characterization and assessment, Radiology, 2007, 244(1):64-77.
Sirol et al, Lipid-rich atherosclerotic plaques detected by gadofluorine-enhanced in vivo magnetic resonance imaging, Circulation, 2004, 109(23):2890-2896.
Sun et al, Facile, efficient approach to accomplish tunable chemistries and variable biodistributions for shell cross-linked nanoparticles, Biomacromolecules, 2008, 9(7):1997-2006.
Sun et al, MicroPET imaging of MCF-7 tumors in mice via unr mRNA-targeted peptide nucleic acids, Bioconjug Chem, 2005, 16(2):294-305.
Tan et al, Imaging of the unstable plaque, Int J Cardiol, 2008, 127(2):157-165.
Tawakol et al, Noninvasive in vivo measurement of vascular inflammation with F-18 fluorodeoxyglucose positron emission tomography, J Nucl Cardiol, 2005, 12(3):294-301.
Topol et al, Our preoccupation with coronary luminology. The dissociation between clinical and angiographic findings in ischemic heart disease, Circulation, 1995, 92(8):2333-2342.

(Continued)

*Primary Examiner* — David Lukton
(74) *Attorney, Agent, or Firm* — Zackson Law LLC; Saul L. Zackson

(57) ABSTRACT

Tracers comprising an oligopeptide comprising a fragment of a natriuretic peptide, wherein the fragment comprises the sequence Arg-Ile-Asp-Arg-Ile (SEQ ID NO.: 1), and a signaling moiety, are disclosed. Further disclosed are methods of imaging atherosclerotic plaque by PET scanning or MRI using a tracer.

17 Claims, 14 Drawing Sheets

OTHER PUBLICATIONS

Vallabhajosula et al, Atherosclerosis: imaging techniques and the evolving role of nuclear medicine, J Nucl Med, 1997, 38(11):1788-1796.

Worthley et al, In vivo non-invasive serial monitoring of FDG-PET progression and regression in a rabbit model of atherosclerosis, Int J Cardiovasc Imaging, 2009, 25(3):251-257.

Zheng et al, Targeted contrast agent helps to monitor advanced plaque during progression: a magnetic resonance imaging study in rabbits, Invest Radiol, 2008, 43(1):49-55.

Hutchinson et al, Mechanisms of natriuretic-peptide-induced growth inhibition of vascular smooth muscle cells, Cardiovascular Research, 1997, 35:158-167.

Bovy et al, A synthetic linear decapeptide binds to the atrial natriuretic peptide receptors and demonstrates cyclase activation and vasorelaxant activity, J Biol Chem, 1989, 264:20309-20313.

Casco et al, Natriuretic peptide system gene expression in human coronary arteries, J Histochem & Cytochem, 2002, 50:799-809.

Olins et al, A linear analog of atrial natriuretic peptide (ANP) discriminates guanylate cyclase-coupled ANP receptors from non-coupled receptors, J Biol Chem, 1988, 263:10989-10993.

Panteghini, Role and importance of biochemical markers in clinical cardiology, Eur Heart J, 2004, 25:1187-1196.

Willenbrock et al, In vivo measurement of atrial natriuretic peptide receptors using nuclear imaging, Am J Hypertens, 1992, 5:832-836; Abstract Only.

Woodard et al, Expression and control of C-type natriuretic peptide in rat vascular smooth muscle cells, Am J Physiol Regulator Integrative Comp Physiol, 2002, 282:R156-165.

Zavarzin et al, Development of Cu-64 labeled DOTA-cyanocobalamin for PET imaging, J Nucl Med, 2007, 48 (supp 2):316P.

Rossin et al, 64Cu-labeled natriuretic peptide: a promising tracer for atherosclerotic plaque molecular imaging with PET, J Nucl Med, 2007, 48 (supp 2):103P.

* cited by examiner

FIG. 5
FIG. 5A
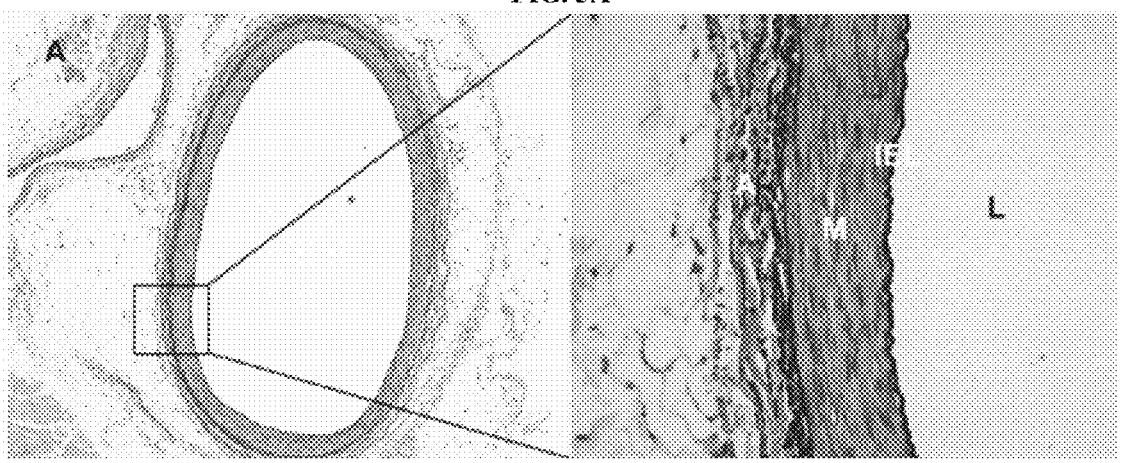
FIG. 5B
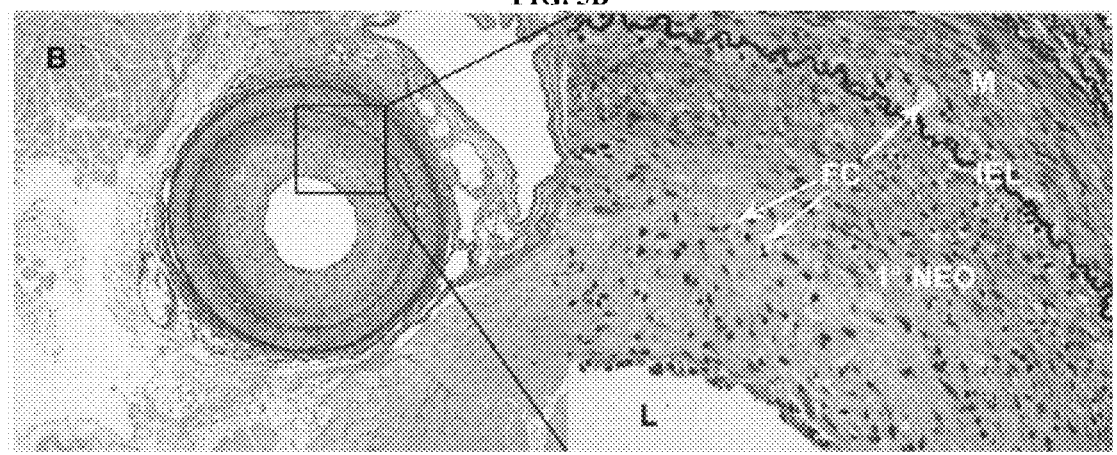

FIG. 10
FIG. 10A
FIG. 10B
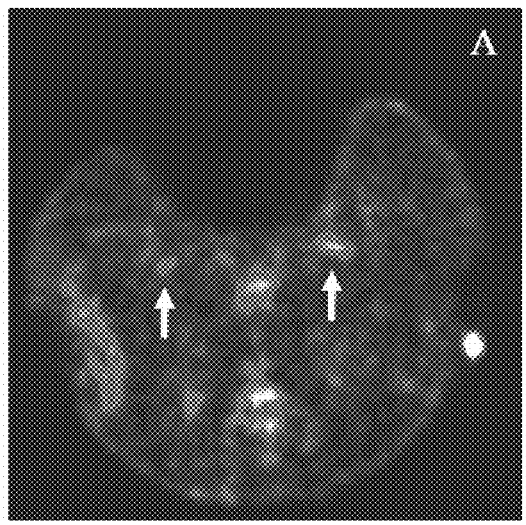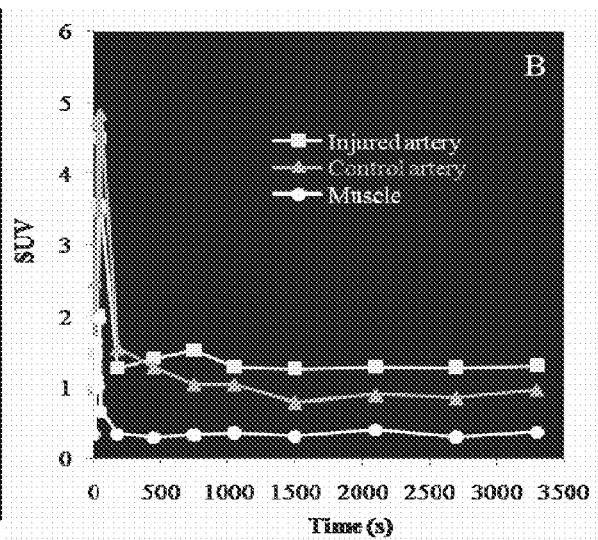
FIG. 10C
FIG. 10D
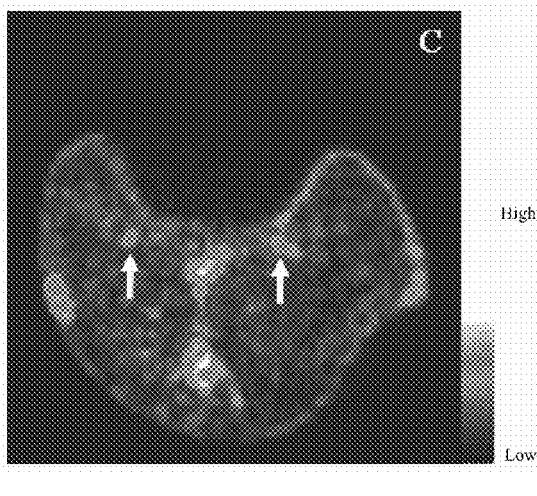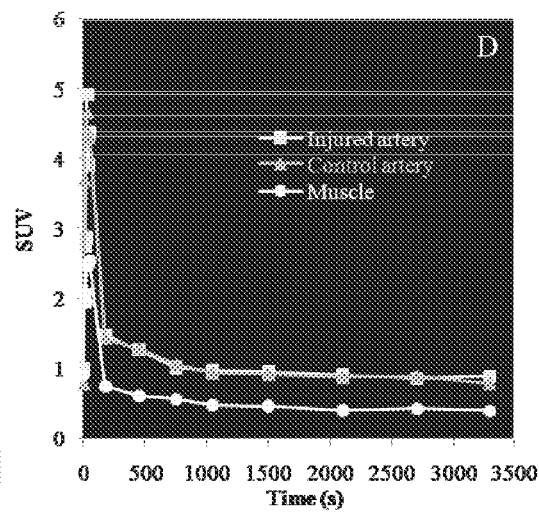

NATRIURETIC PEPTIDE-MEDIATED IMAGING OF ATHEROSCLEROTIC PLAQUE

CROSS-REFERENCE TO RELATED APPLICATIONS

This application claims priority from U.S. Provisional Application Ser. No. 61/130,681, filed on Jun. 2, 2008, which is incorporated herein by reference in its entirety.

GOVERNMENTAL INTEREST

The Invention was made with government support under U.S.P.H.S. Grant U01 HL080729, awarded by the National Institutes of Health. The U.S. Government has certain rights in the invention.

INCORPORATION BY REFERENCE OF SEQUENCE LISTING

The Sequence Listing, which is a part of the present disclosure, includes a computer readable form and a written sequence listing comprising nucleotide and/or amino acid sequences. The sequence listing information recorded in computer readable form is identical to the written sequence listing. The subject matter of the Sequence Listing is incorporated herein by reference in its entirety.

INTRODUCTION

Cardiovascular disease is the leading cause of death worldwide despite primary and second prevention. Each year, more than 1 million people in the United States and over 19 million people worldwide experience a sudden cardiac event (acute coronary syndromes and/or sudden cardiac death). A large portion of these individuals have had no prior symptoms.

Atherosclerosis is a systemic disease characterized by accumulation of lipids, inflammatory cells, and connective tissue within the arterial wall. It is a chronic, progressive disease with a long asymptomatic phase. Atherosclerotic plaque exists in at least two forms: unstable ("soft") plaque, and calcified plaque.

Soft plaque can rupture; such ruptures can lead to rapid death. Rupture of an atherosclerotic plaque accounts for approximately 70% of the severe clinical events such as fatal acute myocardial infarction and/or sudden coronary death. Biomarkers for plaque, and methods of imaging plaque, have been investigated (Collinson, P. O., et al., Med. Principles and Practice 16: 247-261, 2007; Collinson, P. O., et al., Heart, Lung and Circulation 16: S71-S82, 2007; Apple, F. W., et al., Clinical Chemistry 51: 810-824, 2005).

Positron emission tomography (PET) has been used for plaque imaging. (Langer H F, et al. J Am Coll Cardiol. 52:1-12, 2008; Davies J R, et al. J Nucl Med., 45:1898-1907, 2004) To date, many PET radiotracers have been evaluated for imaging of atherosclerosis (Davies J R, et al. J Nucl Med., 45:1898-1907, 2004) including fluorine-18-fluorodeoxyglucose (FDG). Rudd J H, et al. J Nucl Med. 49:871-878, 2008. Ogawa M, et al. J Nucl Med. 45:1245-1250, 2004; Rudd J H, et al. Circulation 105:2708-2711, 2002)

Uptake of FDG in the aortic wall of patients with atherosclerosis has been attributed to infiltration of macrophages, smooth muscle cells, and lymphocytes within active atherosclerotic lesions. (Tawakol A, et al. J Nucl Cardiol, 12:294-301, 2005) However, FDG accumulates in all metabolically active tissues and at sites of inflammation in addition to at atherosclerotic plaques. Therefore FDG does not provide differential imaging of vulnerable (soft) atherosclerotic plaques. (Laurberg J M, et al. Atherosclerosis 192:275-282, 2007)

Additional markers for imaging atheleroscloretic plaques include markers of degradation of the extracellular matrix and cell apoptosis including protease derivatives (cathepsin and matrix metalloproteinases) or annexin-V derivatives. (Jaffer F A, et al. J Am Coll Cardiol. 47:1328-1338, 2006) Also, angiogenesis markers such as, integrins, VEGF, and VCAM-1 are currently under evaluation for imaging vulnerable plaque with PET (Beer A J, et al. Cancer Metastasis Rev. 27:631-644, 2008).

Imaging of receptors with atrial natriuretic peptide in animal models has been accomplished using 123I-labeled atrial natriuretic peptide and gamma scintigraphy (Lambert, R., et al. J. Nuclear Medicine 35: 628-637, 1994). However, this technique has not been extended to imaging atherosclerotic plaque.

Natriuretic peptides (NP) are another group of markers that appear to show promise for the detection of atherosclerotic plaque. The NP family consists of three known members: the atrial natriuretic peptide (ANP), brain natriuretic peptide (BNP), and C-type natriuretic peptide (CNP).

The NPs interact with specific cell-surface NP receptors (NPR). (Maack, T., Arq. Bras. Endocrinol. Metabol. 50:198-207, 2006; Hobbs, A., et al. Circulation 110: 1231-1235, 2004; Scotland R S, et al. Proc Natl Acad Sci USA. 102: 14452-14457, 2005) Of the three existing NPRs, the 'clearance receptor' (NPR-C) represents approximately 95% of the entire NPR population and is expressed during the growth and remodeling of vascular smooth muscle cells. (Maack, T., Annu Rev Physiol. 54:11-27, 1992) In addition, NPR-C is the only NPR that recognizes all the NPs and NP fragments containing as few as five conserved contiguous amino acids (Arg-Ile-Asp-Arg-Ile, SEQ ID NO.: 1). (Hobbs. A, et al. Circulation. 110: 1231-1235, 2004) In humans, the expression of NPR-C is up-regulated in atherosclerotic plaques. (Casco, V. H., et al. J Histochem Cytochem. 50:799-809, 2002; Naruko, T., et al. Circulation 94: 3103-3108, 1996) The presence of high levels of CNP and NPR-C in the neointima of atherosclerotic-like plaques has been demonstrated in several animal models that mimic human athlerosclerosis. (Brown, J., et al. Am J Physiol. 272: H2919-2931, 1997; Brown, J., et al. Circ. Res. 77: 906-918, 1995; Leidenfrost, J. E., et al. Am J Pathol. 163: 773-778, 2003)

A C-type atrial natriuretic factor (C-ANF) has been disclosed that binds to NPR-C. (Hobbs, A., et al., Circulation 110: 1231-1235, 2004; Maack, T., Annu Rev Physiol. 54: 11-27, 1992; Maack, T., et al. Science 238: 675-678, 1987; Zheng, J., et al. Invest Radiol. 43: 49-55, 2008).

SUMMARY

The present inventors describe herein tracers which can be used for imaging distribution of natriuretic peptide receptors, including receptors which bind C-type atrial natriuretic factor (C-ANF). In some embodiments, these tracers can be used for imaging distribution of atherosclerotic plaque, in particular unstable plaque, and can also be used for distinguishing between unstable and stable plaque. In various embodiments, the tracers described herein can be used as probes for imaging atherosclerotic plaque using positron emission tomography (PET) scanning or magnetic resonance imaging (MRI).

Hence, in some embodiments, the present teachings disclose tracer molecules. A tracer of these embodiments comprises an oligopeptide comprising a fragment of a natriuretic peptide, and a signaling moiety. In some aspects, a tracer can comprise an oligopeptide which can have the sequence of a C-type atrial natriuretic peptide or a fragment thereof. In various configurations, such oligopeptides can comprise the sequence Arg-Ile-Asp-Arg-Ile (SEQ ID NO: 1). In some embodiments, an oligopeptide fragment can be less than a full-length natriuretic peptide. A tracer comprising such oligopeptide fragments can be, in various configurations, a tracer which does not induce vasodilation or cause a drop in blood pressure in a subject following administration to the subject in an amount effective for imaging atherosclerotic plaque distribution by positron emission tomography (PET) scanning. A tracer comprising such oligopeptide fragments can be, in various configurations, a tracer which does not induce vasodilation or cause a drop in blood pressure in a subject following administration to the subject in an amount effective for imaging atherosclerotic plaque distribution by magnetic resonance imaging (MRI) scanning.

In other embodiments, the present teachings disclose imaging methods. In various aspects, these include methods of determining distribution of atherosclerotic plaque in a subject; methods of determining distribution of unstable atherosclerotic plaque in a subject; methods of determining risk in a subject of impending plaque rupture; and methods of determining distribution of C-type atrial natriuretic peptide in a subject. A subject of these methods can be any mammal, including a human, such as a human having, or at risk of developing, an atherosclerotic plaque such as an unstable ("soft") plaque, a human at risk for rupturing an atherosclerotic plaque such as an unstable plaque, a human in the process of rupturing a soft atherosclerotic plaque, and/or a human having, or at risk for developing, a stable (calcified) plaque.

In various configurations, an oligopeptide of the present teachings can include at least 2 cysteine residues, which can comprise, in various configurations, at least one cystine (i.e., include a disulfide bridge). In some other configurations, the cysteines can be in reduced form (i.e., does not include a disulfide bridge).

In some configurations, an oligopeptide comprised by a tracer can be no greater than about 20 amino acids in length. In some configurations, an oligopeptide comprised by a tracer can comprise the sequence Cys-Phe-Gly-Gly-Arg-Ile-Asp-Arg-Ile-Gly-Ala-Cys-NH$_2$ (SEQ ID NO: 2), in which the carboxy terminal cysteine is aminated. In some configurations, the cysteines of this sequence can comprise a disulfide linkage (a cysteine).

In various configurations, an oligopeptide of these embodiments can be no greater than 25 amino acids, no greater than 24 amino acids, no greater than 23 amino acids, no greater than 22 amino acids, no greater than 21 amino acids, no greater than 20 amino acids, no greater than 19 amino acids, no greater than 18 amino acids, no greater than 17 amino acids, no greater than 16 amino acids, no greater than 15 amino acids, no greater than 14 amino acids, no greater than 13 amino acids, no greater than 12 amino acids, no greater than 11 amino acids, or no greater than 10 amino acids in length. In some configurations, the cysteines of these oligopeptides can comprise a cysteine comprising a disulfide bridge, or can be in the reduced, free sulfhydryl form. In addition, an oligopeptide of a tracer can further comprise a sequence unrelated to natriuretic peptide, and/or can further comprise one or more non-peptidyl components such as a polymer such as an polyethylene glycol.

Accordingly, in various aspects, the present teachings disclose tracers comprising an oligopeptide and a signaling moiety. An oligopeptide moiety of these aspects can comprise a fragment of a natriuretic peptide, wherein the fragment comprises the sequence Arg-Ile-Asp-Arg-Ile (SEQ ID NO: 1). An oligopeptide moiety can comprise a cysteine, and can comprise the sequence Cys-Phe-Gly-Gly-Arg-Ile-Asp-Arg-Ile-Gly-Ala-Cys-NH$_2$, (SEQ ID NO: 2) and can be no greater than about 25 amino acids in length.

In some configurations, an oligopeptide moiety can be no greater than 20 amino acids in length, no greater than 19 amino acids in length, no greater than 18 amino acids in length, no greater than 17 amino acids in length, no greater than 16 amino acids in length, no greater than 15 amino acids in length, no greater than 14 amino acids in length, no greater than 13 amino acids in length, no greater than 12 amino acids in length, no greater than 11 amino acids in length, or no greater than 10 amino acids in length. In some configurations, the cysteine residues can comprise a cysteine. In some configurations, the oligopeptide moiety can be a fragment of a natriuretic peptide and consist of the sequence H-Arg-Ser-Ser-c[Cys-Phe-Gly-Gly-Arg-Ile-Asp-Arg-Ile-Gly-Ala-Cys]-NH$_2$ (SEQ ID NO: 3).

In some configurations, a tracer can comprise a radionuclide such as a positron emitter. A positron-emitting radionuclide of these configurations can be, without limitation, carbon-11, nitrogen-13, oxygen-14, oxygen-15, fluorine-18, iron-52, copper-62, copper-64, zinc-62 zinc-63, gallium-68, arsenic-74, bromine-76, rubidium-82, yttrium-86, zirconium-89, technetium-94m, indium-110m, iodine-122, iodine-123, iodine-124, iodine-131, or cesium-137. In some configurations, a radionuclide can be selected from carbon-11, nitrogen-13, oxygen-15, fluorine-18, iron-52, copper-64, gallium-68, yttrium-86, bromine-76, zirconium-89, iodine-123, and iodine-124. In other configurations, a positron emitter can be selected from carbon-11, nitrogen-13, oxygen-15, fluorine-18, and copper-64. In some configurations, a radionuclide can be copper-64.

In various configurations, a radionuclide can be comprised by a carrier moiety, such as a chelating agent. In some configurations, a carrier moiety can be, without limitation, a dodecanetetraacetic acid such as 1,4,7,10-tetraazacyclododecane-1,4,7,10-tetracetic acid (DOTA).

In some configurations, the signaling moiety of a tracer can be a T1 relaxation time-reducing agent, such as gadolinium, manganese or iron. In some configurations, the T1 relaxation time-reducing agent can be a gadolinium.

In some configurations, the signaling moiety of a tracer can be a T2 relaxation time-reducing agent. In some configurations, the T2 relaxation time-reducing agent can be a superparamagnetic iron oxide (SPIO) or an ultrasmall superparamagnetic iron oxide (USPIO).

In various configurations, the present teachings include methods of determining distribution of atherosclerotic plaque in a subject. These methods can comprise administering a tracer to the subject; and subjecting the subject to positron emission tomography (PET) scanning using a tracer comprising a positron-emitting radionuclide, or MRI scanning, using a tracer comprising a T1 relaxation time-reducing agent or a T2 relaxation time-reducing agent.

In various configurations, the present teachings include methods of determining distribution of unstable atherosclerotic plaque in a subject. These methods can comprise administering a tracer to the subject; and subjecting the subject to positron emission tomography (PET) scanning using a tracer comprising a positron-emitting radionuclide, or MRI scanning, using a tracer comprising a T1 relaxation time-reducing agent or a T2 relaxation time-reducing agent.

In various configurations, the present teachings include methods of determining risk in a subject of impending plaque rupture. These methods can comprise administering a tracer to the subject; and subjecting the subject to positron emission tomography (PET) scanning using a tracer comprising a positron-emitting radionuclide, or MRI scanning, using a tracer comprising a T1 relaxation time-reducing agent or a T2 relaxation time-reducing agent.

In various configurations, the present teachings include methods of determining distribution of C-type atrial natriuretic peptide receptors in a subject. These methods can comprise administering a tracer to the subject; and subjecting the subject to positron emission tomography (PET) scanning using a tracer comprising a positron-emitting radionuclide, or MRI scanning, using a tracer comprising a T1 relaxation time-reducing agent or a T2 relaxation time-reducing agent.

The present teachings include the following aspects:

1. A tracer comprising:
    an oligopeptide comprising a fragment of a natriuretic peptide, wherein the fragment comprises the sequence Arg-Ile-Asp-Arg-Ile (SEQ ID NO: 1); and
    a positron-emitting radionuclide.
2. A tracer in accordance with aspect 1, wherein the fragment of a natriuretic peptide comprises the sequence Cys-Phe-Gly-Gly-Arg-Ile-Asp-Arg-Ile-Gly-Ala-Cys-NH$_2$, (SEQ ID NO.: 2).
3. A tracer in accordance with aspect 1, wherein the fragment of a natriuretic peptide comprises a disulfide bond and the sequence comprises the sequence H-Arg-Ser-Ser-c[Cys-Phe-Gly-Gly-Arg-Ile-Asp-Arg-Ile-Gly-Ala-Cys]-NH$_2$ (SEQ ID NO.: 3).
4. A tracer in accordance with aspect 1, wherein the positron-emitting radionuclide is selected from the group consisting of carbon-11, nitrogen-13, oxygen-14, oxygen-15, fluorine-18, iron-52, copper-62, copper-64, zinc-62, zinc-63, gallium-68, arsenic-74, bromine-76, rubidium-82, yttrium-86, zirconium-89, technetium-94m, indium-110m, iodine-122, iodine-123, iodine-124, iodine-131, cesium-137.
5. A tracer in accordance with aspect 4, wherein the positron-emitting radionuclide is selected from the group consisting of carbon-11, nitrogen-13, oxygen-15, fluorine-18, iron-52, copper-64, gallium-68, yttrium-86, bromine-76, zirconium-89, iodine-123, and iodine-124.
6. A tracer in accordance with aspect 5, wherein the positron-emitting radionuclide is selected from the group consisting of carbon-11, nitrogen-13, oxygen-15, fluorine-18, and copper-64.
7. A tracer in accordance with aspect 6, wherein the positron-emitting radionuclide is a copper-64.
8. A tracer in accordance with aspect 7, further comprising a radionuclide carrier moiety.
9. A tracer in accordance with aspect 8, wherein the carrier moiety is a dodecanetetraacetic acid (DOTA).
10. A method of determining distribution of C-type atrial natriuretic peptide receptors in a subject, comprising:
    administering to the subject a tracer comprising a) an oligopeptide comprising a fragment of a natriuretic peptide, wherein the fragment comprises the sequence Arg-Ile-Asp-Arg-Ile (SEQ ID NO.: 1) and b) a positron-emitting radionuclide; and
    subjecting the subject to positron emission tomography scanning.
11. A method in accordance with aspect 10, wherein the fragment of a natriuretic peptide comprises the sequence Cys-Phe-Gly-Gly-Arg-Ile-Asp-Arg-Ile-Gly-Ala-Cys-NH$_2$, (SEQ ID NO.: 2).
12. A method in accordance with aspect 10, wherein the fragment of a natriuretic peptide comprises a disulfide bond and the sequence comprises the sequence H-Arg-Ser-Ser-c [Cys-Phe-Gly-Gly-Arg-Ile-Asp-Arg-Ile-Gly-Ala-Cys]-NH$_2$ (SEQ ID NO.: 3).
13. A method in accordance with aspect 10, wherein the positron-emitting nuclide is selected from the group consisting of carbon-11, nitrogen-13, oxygen-14, oxygen-15, fluorine-18, iron-52, copper-62, copper-64, zinc-62, zinc-63, gallium-68, arsenic-74, bromine-76, rubidium-82, yttrium-86, zirconium-89, technetium-94m, indium-110m, iodine-122, iodine-123, iodine-124, iodine-131, cesium-137.
14. A method in accordance with aspect 11, wherein the positron-emitting radionuclide is selected from the group consisting of carbon-11, nitrogen-13, oxygen-15, fluorine-18, iron-52, copper-64, gallium-68, yttrium-86, bromine-76, zirconium-89, iodine-123, and iodine-124.
15. A method in accordance with aspect 11, wherein the positron-emitting radionuclide is selected from the group consisting of carbon-11, nitrogen-13, oxygen-15, fluorine-18, and copper-64.
16. A method in accordance with aspect 13, wherein the positron-emitting radionuclide is a copper-64.
17. A method of imaging atherosclerotic plaque in a subject, comprising imaging distribution of C-type atrial natriuretic peptide receptors in the subject in accordance with aspect 10.
18. A method of imaging atherosclerotic plaque in a subject in accordance with aspect 15, wherein the atherosclerotic plaque is unstable atherosclerotic plaque.
19. A method of determining risk in a subject of impending plaque rupture, comprising imaging distribution of C-type atrial natriuretic peptide receptors in the subject in accordance with aspect 10.

BRIEF DESCRIPTION OF THE DRAWINGS

FIG. 10 presents PET images showing specific binding of $^{64}$Cu-DOTA-C-ANF to injured arteries on test animals.

DETAILED DESCRIPTION

Figure 1:
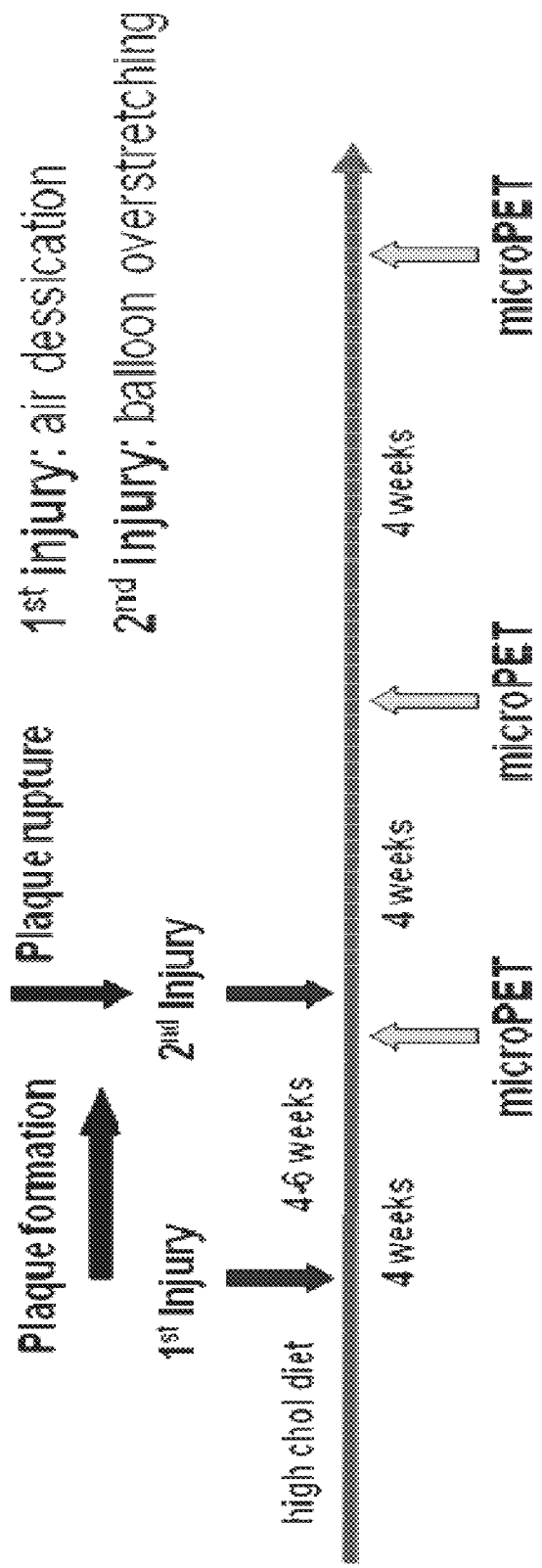
FIG. 1 illustrates an animal model of atherosclerosis using New Zealand rabbits.

The present inventors have developed tracers which can be used for imaging atherosclerotic plaque by either positron emission tomography (PET) scanning or magnetic resonance imaging (MRI) scanning. Each tracer comprises an oligopeptide moiety and a signaling moiety. In various configurations, an oligopeptide moiety can be a fragment of a natriuretic peptide which does not contain the entire amino acid sequence of a full length natriuretic peptide. In various embodiments, an oligopeptide moiety can comprise the sequence Arg-Ile-Asp-Arg-Ile (SEQ ID NO: 1). In various configurations, the oligopeptide moiety can comprise, for example, no more than 25 amino acids of a full length natriuretic peptide, no more than 24 amino acids of a full length natriuretic peptide, no more than 23 amino acids of a full length natriuretic peptide, no more than 22 amino acids of a full length natriuretic peptide, no more than 21 amino acids of a full length natriuretic peptide, no more than 20 amino acids of a full length natriuretic peptide, no more than 19 amino acids of a full length natriuretic peptide, no more than 18 amino acids of a full length natriuretic peptide, no more than 17 amino acids of a full length natriuretic peptide, no more than 16 amino acids of a full length natriuretic peptide, no more than 15 amino acids of a full length natriuretic peptide, no more than 14 amino acids of a full length natriuretic peptide, no more than 13 amino acids of a full length natriuretic peptide, no more than 12 amino acids of a full length natriuretic peptide, no more than 11 amino acids of a full length natriuretic peptide, no more than 10 amino acids of a full length natriuretic peptide, no more than 9 amino acids of a full length natriuretic peptide, no more than 8 amino acids of a full length natriuretic peptide, no more than 7 amino acids of a full length natriuretic peptide, no more than 6 amino acids of a full length natriuretic peptide, or no more than 5 amino acids of a full length natriuretic peptide. The natriuretic peptide can be an atrial natriuretic peptide. In some embodiments, the peptide can be a C-type atrial natriuretic peptide. The natriuretic peptide can be a human atrial natriuretic peptide.

In various embodiments, a signaling moiety of a tracer described can be any signaling moiety effective for providing a detectable signal using PET scanning. For PET, a signaling moiety can be any positron-emitting isotope known to skilled artisans. In various embodiments, a signaling moiety of a tracer described can be any signaling moiety effective for providing a detectable signal using MRI. In these embodiments, a signaling moiety can be any T1 relaxation time-reducing agent, or any T2 relaxation time-reducing agent known to skilled artisans.

The methods and compositions described herein utilize laboratory techniques well known to skilled artisans, and can be found in laboratory manuals such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; and Harlow, E., Using Antibodies: A Laboratory Manual, Cold Spring Harbor Laboratory Press, Cold Spring Harbor, N.Y., 1999; and textbooks such as Hedrickson et al., Organic Chemistry 3rd edition, McGraw Hill, N.Y., 1970. Synthesis of tracers, including synthesis of oligopeptides, can be accomplished using routine methods well know to skilled artisans. In some cases, oligopeptides can be obtained from a commercial supplier, such as, for example, (Cys18)-Atrial Natriuretic Factor (4-18) amide (rat; Code H-3134) from Bachem (Torrence, Calif.) Pharmaceutical methods and compositions described herein, including methods for determination of effective amounts for imaging, and terminology used to describe such methods and compositions, are well known to skilled artisans and can be adapted from standard references such as Remington: the Science and Practice of Pharmacy (Alfonso R. Gennaro ed. 19th ed. 1995); Hardman, J. G., et al., Goodman & Gilman's The Pharmacological Basis of Therapeutics, Ninth Edition, McGraw-Hill, 1996; and Rowe, R. C., et al., Handbook of Pharmaceutical Excipients, Fourth Edition, Pharmaceutical Press, 2003. As used in the present teachings and the appended claims, the singular forms "a", "an" and "the" are intended to include the plural forms as well, unless the context indicates otherwise.

EXAMPLES

In the following examples, the present inventors describe an animal model that produces atherosclerotic plaques. The presence of NPR-C receptor on the neointimal surface has been confirmed by IHC. In addition, a $^{64}$Cu-labeled tracer for non-invasive imaging of the NPR-C with PET has been produced. Small animal imaging studies with PET show $^{64}$Cu-DOTA-C-ANF$_{4-18}$ uptake at the injury site in vivo. Blocking studies show that the binding is receptor specific. Imaging at various time points indicates an increase in activity in plaques that are unstable, thus providing a method of distinguishing stable and unstable plaques.

The following examples are intended to be illustrative of various embodiments of the present teachings and are not intended to be limiting of the scope of any claim.

Example 1

This example discloses the materials and methods that were used in the examples described herein.
Synthesis of DOTA-C-ANF C-ANF (rat ANF(4-23), des-Gln18, des-Ser19, des-Gly20, 22, des-Leu21) was purchased from Bachem, Calif., and 1,4,7,10-tetraazacyclododecane-1,4,7,10-tetraacetic acid mono (N-hydroxysuccinimide ester (DOTA) was purchased from Macrocyclics, Tex. The conjugation was carried out following standard procedures. (Rossin R, et al. J Nucl Med. 49:103-111, 2008) The DOTA-conjugated C-ANF was separated from unbound DOTA and from unconjugated peptide by solid phase extraction (C-18 Sep-Pak cartridges, Waters, Mass.) and reverse phase high performance liquid chromatography (RP-HPLC), respectively. The purified $^{64}$Cu-OTA-C-ANF was concentrated with Speed-Vac (SC 100, Savant, Minn.) and refrigerated vapor trap (RVT4104, Savant, Minn.). RP-HPLC was performed on a Dionex system (Dionex, Calif.) equipped with an UV-Vis detector (Dionex, Calif.) and a BioScan B-FC-3200 radioisotope detector (BioScan Inc., Washington, D.C.) on a C-18 analytical column (5 μm, 4.6 mm×220 mm, Perkin Elmer, Mass.), with a linear gradient (from 100% H2O to 65% acetonitrile in 45 min) at a flow rate of 1 ml/min. The UV absorbance was monitored at 210 nm. Under these conditions, C-ANF and DOTA-C-ANF elute from the column at 25.6 and 28.2 min, respectively. The conjugation efficiency was more than 95%, as determined by RP-HPLC The presence of one DOTA per peptide was confirmed by liquid chromatography-electro spray ionization mass spectrometry (LC-ESI-MS) (Waters 2695 separation and Micromass ZQ module, Waters, Mass.).
Copper-64 Labeling of DOTA-C-ANF Copper-64 ($^{64}$Cu; $t_{1/2}$=12.7 h, β+=17%, β−=40%) was produced on the Washington University Medical School CS-15 cyclotron by the $^{64}$Ni (p,n) $^{64}$Cu nuclear reaction at a specific activity of 0.74-2.96 GBq/μg at the end of bombardment, as previously described. (McCarthy, D. W., et al. Nucl. Med. Biol. 24: 35-43, 1997) DOTA-C-ANF (10 μg, about 5 nmol) was labeled with $^{64}$Cu (0.37 GBq) in 200 μL 0.1M ammonium acetate buffer (pH 5.5) at 43° C. for 1 h with a yield of 78.5±4.8% (n=10). The crude solution was purified with C-18 sep-pak, and then further diluted with saline for animal study.

The specific activity of the $^{64}$Cu-DOTA-C-ANF conjugate was 58.1±3.6 MBq/nmol. The identity of $^{64}$Cu-DOTA-C-ANF was confirmed by LC-MS after decay.

Serum Stability of $^{64}$Cu-DOTA-C-ANF

The stability of $^{64}$Cu-DOTA-C-ANF was evaluated in rabbit serum (Sigma-Aldrich, St Louis, Mo.). After incubation at 37° C. for 1 h, the solution containing the radiotracer was analyzed by radio-HPLC. As a control, a similar amount of $^{64}$Cu-acetate was also incubated in rabbit serum and analyzed by HPLC. The tracer stability in serum was determined from the percentage of intact $^{64}$Cu-DOTA-C-ANF in the radiochromatogram.

Tracer Blood Clearance Study

The blood clearance studies were performed in normal rabbits (n=4) to evaluate the pharmacokinetics of tracer in vivo. About 20 MBq of $^{64}$Cu-DOTA-C-ANF was injected intravenously into the left ear of rabbit, and blood sample (0.2 mL) was drawn from the contralateral ear over the period of 1 h (1 min, 3 min, 5 min, 10 min, 20 min, 40 min and 60 min). The activity of the blood samples were counted in gamma counter and presented in percent injected dose per gram (ID %/g).

Animal Preparations to Induce Atherosclerotic-Like Lesions

All animal studies were performed in compliance with guidelines set forth by the NIH Office of Laboratory Animal Welfare and approved by the Washington University Animal Studies Committee. Complex atherosclerotic-like arterial lesions containing a fibrous cap and a lipid-enriched core, similar to the structure of atheromatous plaques in human arteries, were induced in the right femoral artery of rabbits. Injury was induced by air desiccation and followed by angioplasty at a later time point as reported previously. (Sarembock I J, et al. Circulation. 80:1029-1040, 1989) Briefly, male New Zealand White rabbits were fed 0.25% cholesterol-enriched diet throughout the study and elevated serum cholesterol (>200 mg/dL) was confirmed at the time of vessel injury. The right femoral artery was exposed aseptically through a longitudinal skin incision and lidocaine was applied topically to prevent spasm. A 1-2 cm segment of the vessel was isolated between air-tight ligatures and small branches were ligated with suture. A 27-gauge needle was used to puncture the isolated segment proximally as a vent. A second 27-gauge needle was inserted distally into the segment and nitrogen gas was passed through the vessel at a flow rate of 80 mL/min for 8 min to dry and cause sloughing of the endothelium. The segment was then flushed with saline and the ligatures were released to restore blood flow, with gentle pressure applied to the puncture sites for a few minutes to maintain hemostasis. The skin incision was closed and the animal was recovered from anesthesia.

Four to six weeks after the air dessication-induced injury, the lesion site and extent of stenosis in the femoral artery were identified by an angiogram obtained with use of a 4F guide catheter introduced through a carotid arterial cutdown and advanced to the distal aorta. Heparin (100 U/kg, intravenous) was given to prevent clot formation in the catheters. A 0.014 in guidewire was then advanced across the lesion and the guide catheter was removed. A 2.0–2.5×20 mm coronary angioplasty balloon was advanced over the guidewire and the site of stenosis was dilated with three, 30 s balloon inflations of 6-8 atm with 1 min between inflations. After re-injuring the lesion site, patency of the femoral artery was confirmed by an angiogram through the angioplasty catheter before the catheter was removed. The carotid was ligated, the skin incision closed, and the animal was recovered from anesthesia. The left femoral artery was left uninjured as a control.

Imaging Protocol

The experimental design is schematized in FIG. 1. Tracer uptake: 8 rabbits (weight=4.1±0.5 kg at the time of the first imaging) were imaged by MRI and small animal PET four-to-six weeks after the air dessication induced-injury (time point (TP) 1); 5 rabbits coming from TP 1 were imaged by MRI and small animal PET three weeks after the balloon overstretching induced injury (TP 2); 4 rabbits coming from TP 2 were imaged by MRI and small animal PET four weeks after TP 2 (TP 3). For each PET imaging, about 128±32 MBq (n=21) of purified $^{64}$Cu-DOTA-C-ANF tracer (about 2 nmol) was administered.

Receptor Blocking Studies

Receptor blocking studies were performed on three additional rabbits (4.1±0.34 kg). One-to-three weeks after the second injury, the animals were imaged with MRI and PET for a pre-blocking study to confirm the presence of atherosclerotic lesions and uptake of $^{64}$Cu-DOTA-C-ANF to NPR-C receptor on the plaque. One week later, besides the MRI imaging, the PET blocking studies were performed on the same rabbits scanned in pre-blocking studies by co-injection of $^{64}$Cu-DOTA-C-ANF with a blocking dose of unlabeled C-ANF peptide (1 mg, C-ANF: $^{64}$Cu-DOTA-C-ANF=100:1 mole ratio) and imaged with PET.

The baseline tracer uptake was measured in one healthy rabbit (4.6 kg) on a normal rabbit chow diet. The level of cholesterol in plasma was analyzed in each rabbit before imaging sessions. Samples of injured and control arteries were taken at each TP for histology and immunohistochemistry.

MRI Studies

The presence of atherosclerotic lesions in the rabbits was confirmed by 3T MRI 1 hour after administration of a non-receptor specific plaque-targeting contrast agent (G, 0.5 µmol/kg body weight, Schering AG, Germany). (Sirol M, et al. Circulation. 109:2890-2896, 2004; Zheng, J., et al. Invest Radiol. 43:49-55, 2008; Meding J, et al. Contrast Media Mol Imaging. 2:120-129, gag2007) This agent has been shown to bind to extracellular matrix proteins such as collagen and proteoglycans. For scanning, the rabbit was placed supine into a plastic bed. Three micropipette tubes filled with 0.5 mL Gadofluorine M (Bayer Schering Pharma AG, Berlin) served as fiducial markers, and were taped into position on the bed. At the beginning of the PET study, these tubes were drained of the Gadofluorine by syringe, and refilled with 0.5 mL of $^{64}$Cu to serve as the PET fiducials. These helped to "co-localize" the plaque regions between the two image modalities.

PET Studies

Immediately after the MR scan, the rabbits were injected with $^{64}$Cu-DOTA-C-ANF (3.9±0.9 mCi) and 60 min dynamic scans were acquired on the microPET Focus-220 (Siemens Medical Solutions, Inc., Malvern, Pa.). Fiducial markers attached to the animal bed and filled with a $^{64}$Cu aqueous solution were used to correlate the MRI and MAP reconstructed PET images. In the competitive blocking experiments, 1 mg of C-ANF was co-administered with the radiotracer (100:1 mole ratio of blocking C-ANF to $^{64}$Cu-DOTA-C-ANF).

Data analysis of the microPET images was performed using the manufacturer's software (ASI Pro). The accumulation of $^{64}$Cu-DOTA-C-ANF at the injury site and on the contralateral, non-injured femoral artery (control) was calculated as standardized uptake values (SUVs) in 3D regions of interest (ROIs) by averaging the activity concentration corrected for decay over the contained voxels (multiple image slices) at selected time points post injection. (Sun X, et al.

Bioconjug Chem. 16:294-305; 2005) SUVs were not corrected for partial volume effects.

$$SUV = \frac{\text{Radioactivity concentration in } ROI\ (\mu Ci/cc)}{\text{Injection dose } (\mu Ci) / \text{animal weight(g)}}$$

After the last PET imaging, the animals were euthanized by exsanguination and the femoral vessels were perfusion-fixed in situ with freshly prepared 4% paraformaldehyde. Tissue samples containing the injured and control arteries were harvested for histology and immunohistochemistry.
Histopathology Vessel specimens were embedded in paraffin, step sectioned (10 µm) transversely at 1 mm intervals to approximate the distance between MRI slices, and the sections stained with hematoxylin and eosin (H&E) and Verhoeff's Van Gieson (VVG) stain for elastin. The sections were examined to identify the plaque components including foam cells, and vascular smooth muscle cells.
Immunohistochemistry (IHC)

Immunohistostaining was performed on paraffin embedded sections from both the injured and non-injured arteries in each rabbit. For immunohistochemistry, we used anti-C-type natriuretic peptide receptor antibody (Abgent, San Diego, Calif.; 1:100) revealed by a secondary fluorescein isothiocyanate-conjugated anti-rabbit antibody (Invitrogen, Carlsbad, Calif.; 1:1000). Slides were viewed with a laser scanning microscope (LSM510 META, Carl Zeiss, Jena, Germany) and the image browser (Carl Zeiss, Jena, Germany). Blocking studies for NPR-C were performed by competitively blocking the primary antibody binding by pre-incubation of diluted antibody (NPR-C rabbit, Abgent, San Diego) with the cognate peptide (0.5 mg/mL) overnight at 4° C. prior to IHC staining. Also, absence of primary antibody was used as a negative control.
Statistical Analysis Results are expressed as mean and standard deviation (SD). The 2-tailed paired and unpaired Student's t test were used to test differences within animals (injured artery vs. control artery) and between animals imaged at different time points (such as TP 1 vs. TP 2), respectively. The significance level in all tests was ≦0.05. GraphPad Prism 4.0 was used for all statistical analyses.

Example 2

This example illustrates an animal model of atherosclerosis.

An animal model of atherosclerosis has been developed using New Zealand rabbits (FIG. 1). Atherosclerotic plaque development was induced by feeding the animals a high cholesterol diet and double injuries (air desiccation and balloon overstretch). Various dates in the examples described herein are listed in Table 1 below.

Example 3

This example illustrates blood test results.

Figure 2:
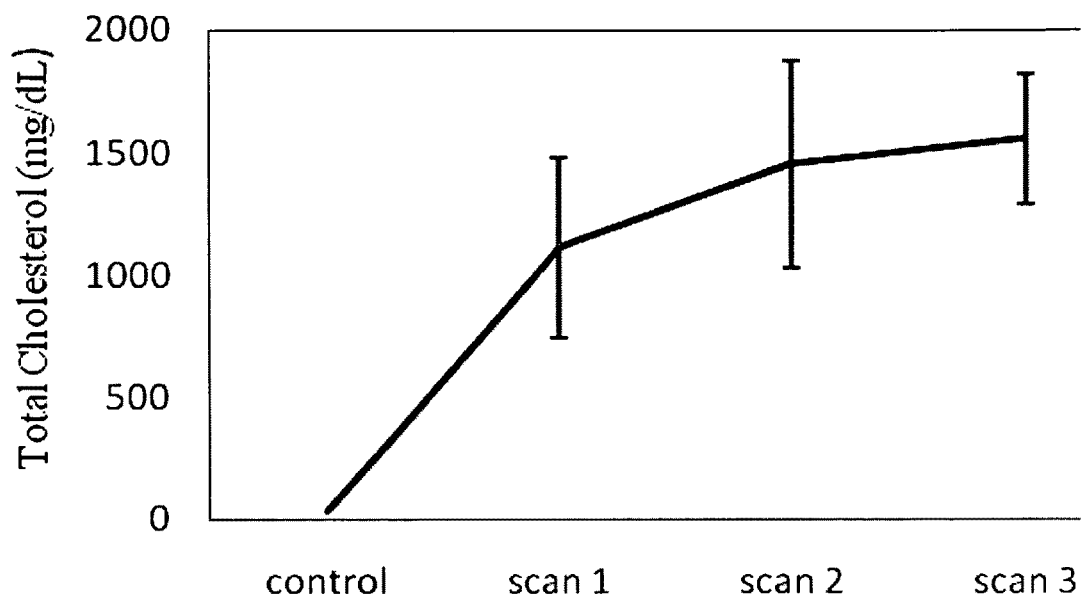
FIG. 2 illustrates lipid panel tests showing an increase of total cholesterol concentration with feeding.

In this example, lipid panel tests were performed at each scan date to make sure cholesterol levels were elevated. Results shown in FIG. 2 show the increase of total cholesterol concentration along with the feeding. Hypercholesteremia was thus confirmed at all imaging time points throughout the study.

Example 4

This example illustrates histology in test animals.

Figure 3:
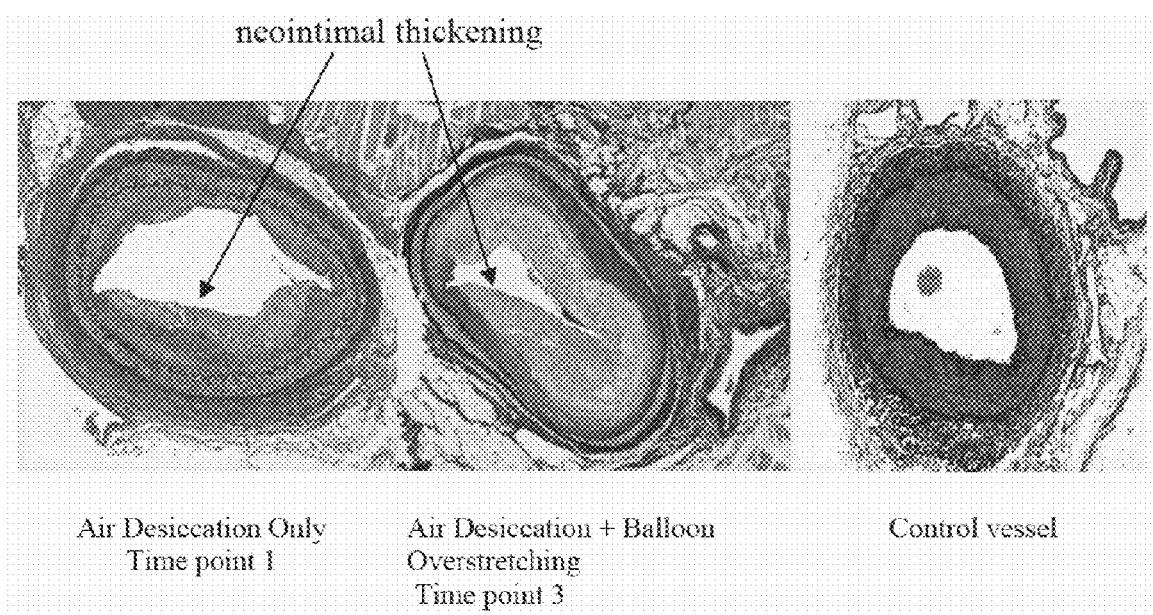
FIG. 3 illustrates a histological analysis that confirms the presence of atherosclerotic-like plaques in an injured vessel, with no plaque formation in a control vessel.

In this example, histological analysis confirms the presence of atherosclerotic-like plaques in the injured vessel, with no plaque formation in the control vessel (FIG. 3).

Example 5

This example illustrates IHC of test animals.

Figure 4:
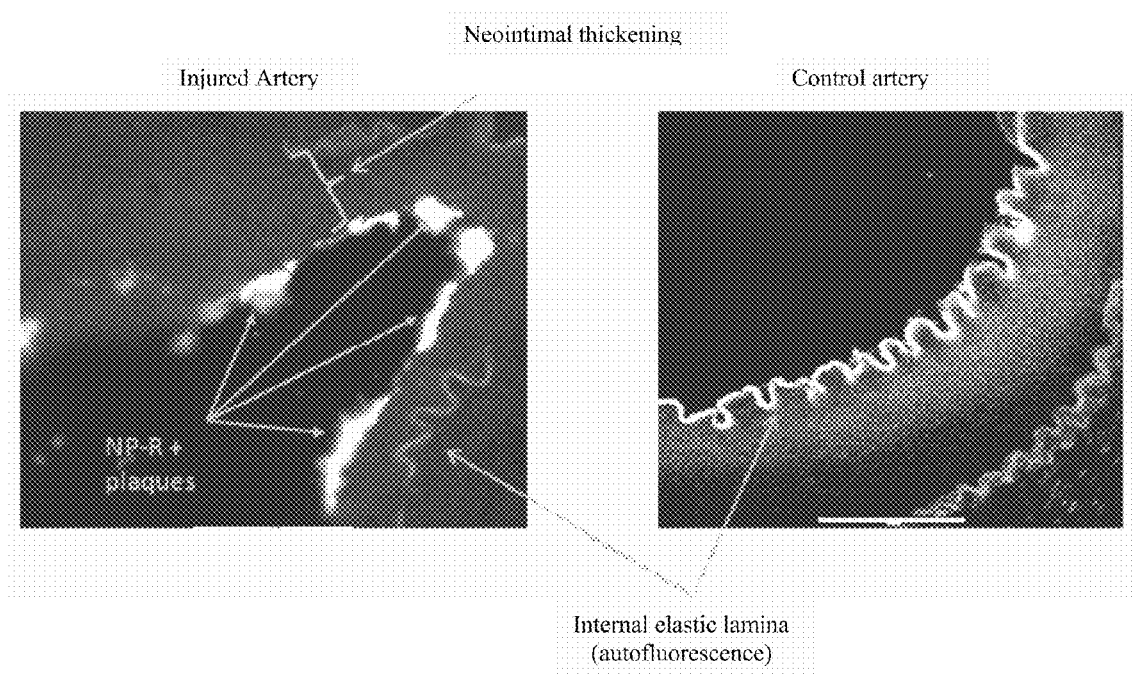
FIG. 4 presents IHC images showing C-type NP receptor presence on the surface of neointima.
Figure 5C:
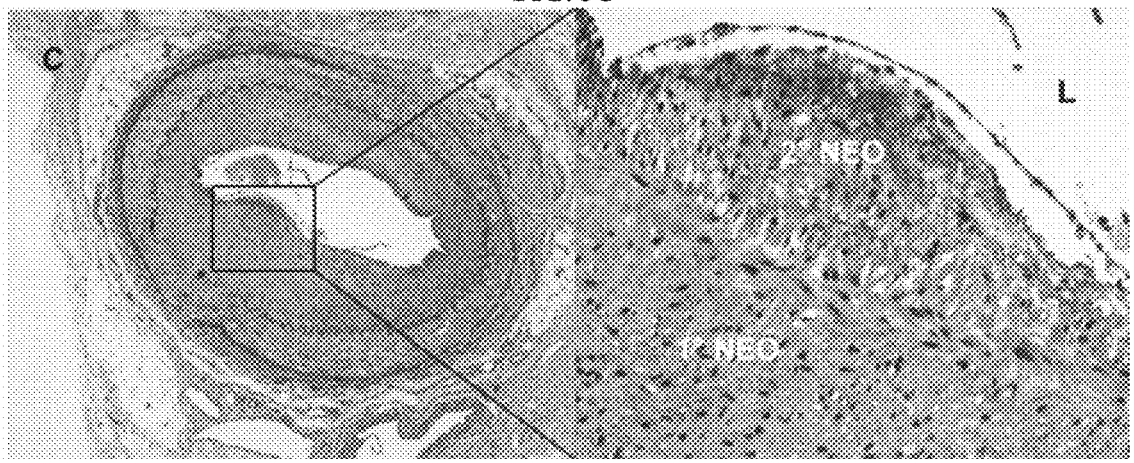
FIG. 5 presents light micrographs of femoral arterial cross-sections from hypercholesterolemic rabbits.
Figure 5D:
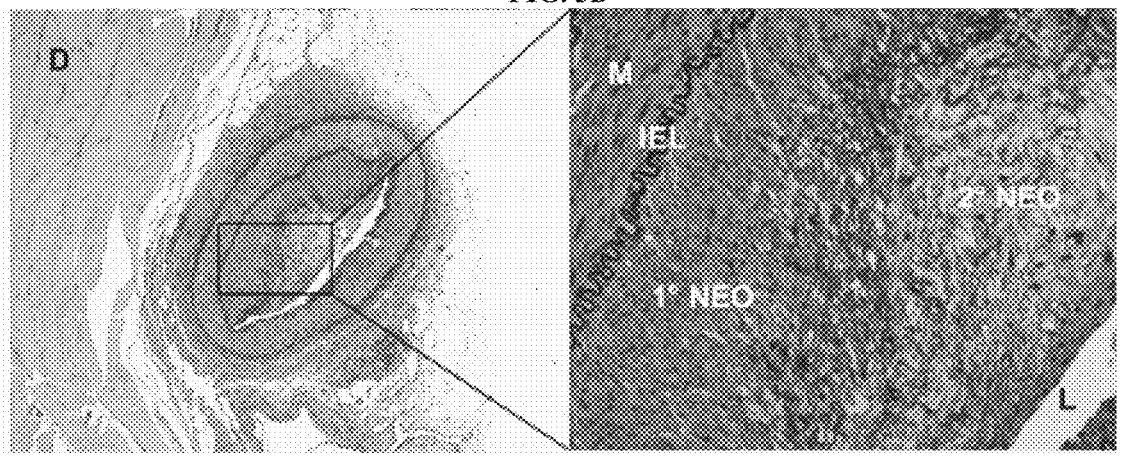
Figure 5E:
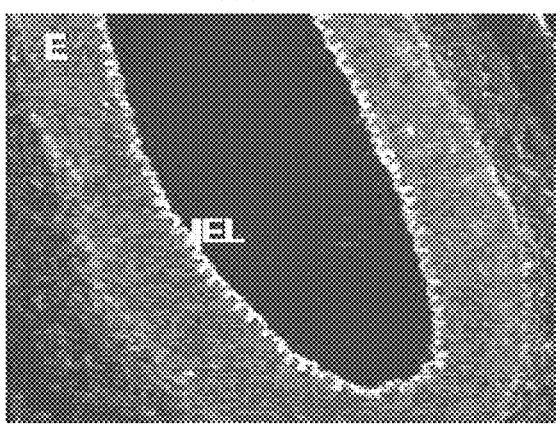
Figure 5F:
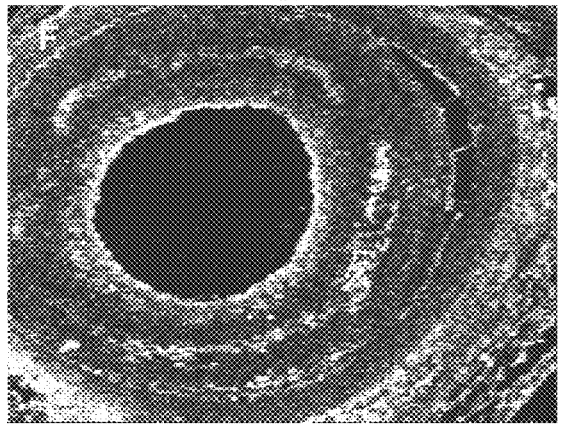
Figure 5G:
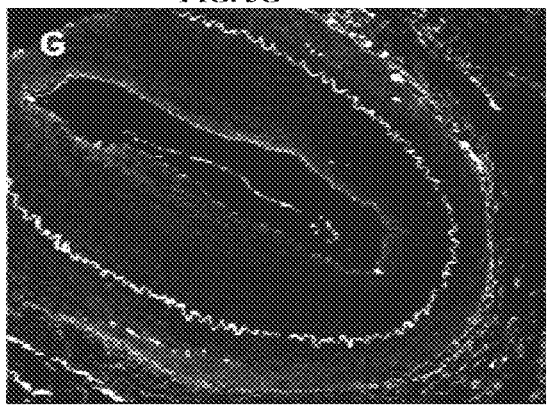
Figure 5H:
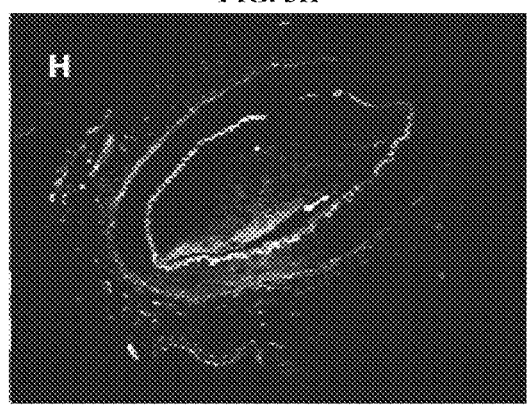
Figure 5I:
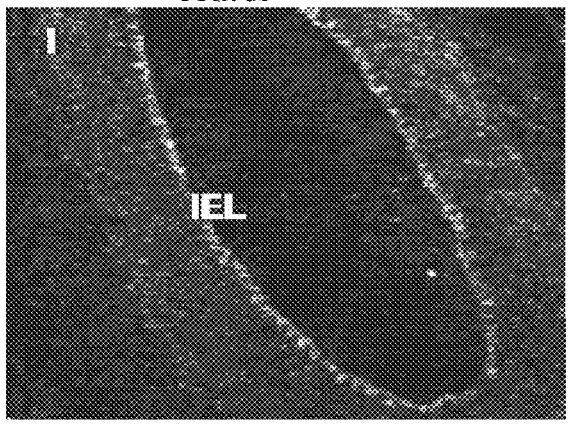
Figure 5J:
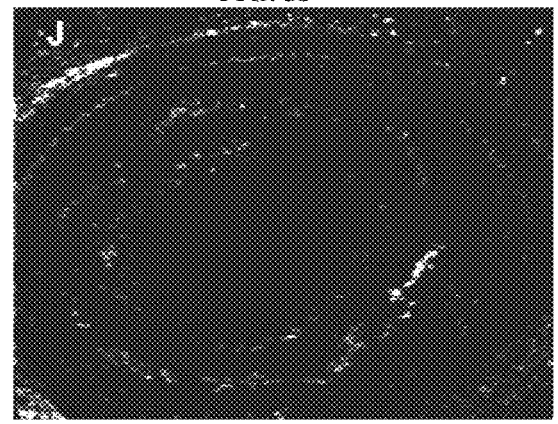

In this example, IHC images obtained on a laser confocal microscope (20×) show C-type NP receptor presence on the surface of the neointima (FIG. 4). The primary antibody is rabbit anti-human polyclonal against the first 100 amino acids of NPR-C. Secondary antibody is FITC-conjugated goat anti-rabbit IgG, affinity purified and blocked with 2% goat serum.

Example 6

This example illustrates histology and IHC of test animals.

FIG. 5 shows light micrographs of femoral arterial cross-sections from hypercholesterolemic rabbits obtained at time points after injury and stained with Verhoeff's Van Gieson (VVG) for elastin (panels A-D) as well as fluorescent images of corresponding sections immunostained for NPR-C (panels E-H) or blocked before immunostaining (panels I and J). Low power micrographs are at 4×, high power insets are 400×. L=lumen.

Panel A shows an uninjured, control femoral artery from the TP 2 rabbit shown in panel C. The inset shows intact internal elastic lamina (IEL), media (M), and adventitia (A). Panel B shows TP 1 4 weeks after air desiccation-induced injury of a femoral artery. The inset shows a primary neointima (1' NEO) containing numerous foam cells (FC) and the dark nuclei of smooth muscle cells. Panel C shows TP2 4 weeks after balloon overstretch injury of a previous air-desication-induced lesion showing a broken IEL (adjacent to inset box) and development of an amorphous, less cellular secondary neointima (2' NEO) shown in the inset. The endothelium is artifactually lifted away from the neointima. Panel D shows TP3 8 weeks after balloon overstretch injury showing enlarged 2' NEO comprised predominantly of matrix and elastin elements with few cells. Panel E shows an uninjured, control femoral artery showing only IEL autofluorescence. Panel F shows TP 1 showing increased fluorescence near the luminal or endothelial surface of the 1' NEO (arrow). Panels G and H show TP2 and TP3 and some fluorescence on the less cellular secondary 2' NEO, but not as much as seen at TP 1. In all immunostained images, the IEL demonstrates autofluorescence. Panel I shows an uninjured, control femoral artery immunofluorescence after competitive blocking of the antibody-antigen binding shows no difference in comparison to the pre-blocked image. Panel J shows TP1 immunofluorescence after competitive blocking of the antibody-antigen binding indicating the specific binding to NPR-C.

Example 7

This example depicts an MRI of a typical atherosclerotic lesion in a test animal.

Figure 6:
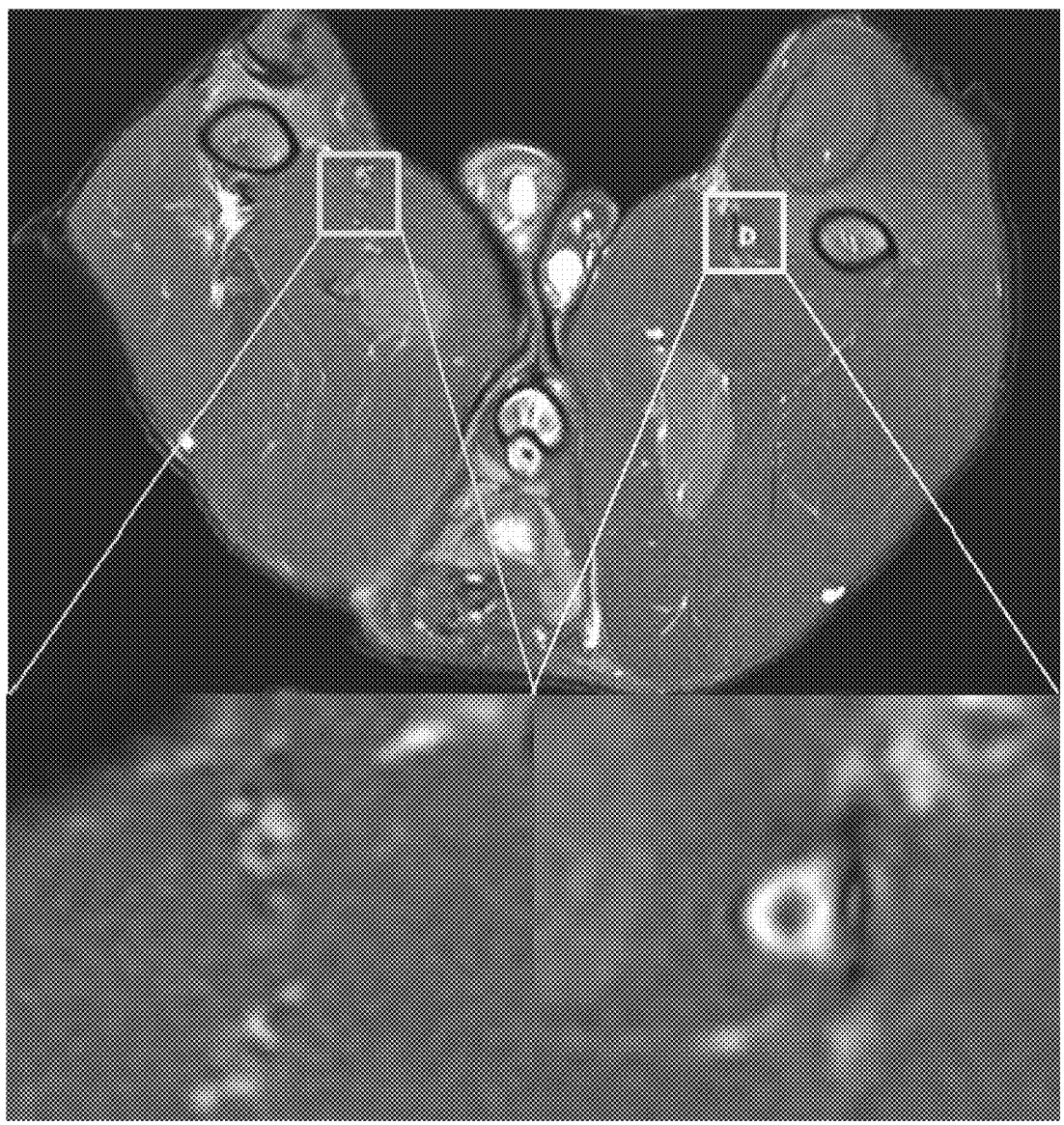
FIG. 6 presents a MR T1 W coronal image of an atherosclerotic lesion.

In this example, a MR T1 W coronal image of a typical atherosclerotic lesion in the femoral artery of a rabbit 4 weeksafter air dessication-induced injury (TP 1) is shown (FIG. 6).

Gadofluorine M (0.5 μmol/kg body weight) was given 1 h before the scan. FIG. 6 shows binding of Gadofluorine M to the injured femoral artery (right box and enlargement) and contrast with the surrounding tissue and femoral vein. The control artery (left box and enlargement) shows weak uptake of the contrast agent. MRI confirmed the presence of a thickened neointima in the injured vessel characteristic of the atherosclerotic-like plaques induced in this model.

Example 8

This example illustrates development of a tracer of the present teachings.

We have chosen C-type atrial natriuretic factor (C-ANF$_{14-18}$, containing the Arg-Ile-Asp-Arg-Ile sequence; SEQ ID NO.: 1) as an agonist of CNP fragment for targeting the clearance NP receptor (NPR-C) expressed on atherosclerotic plaque. We have evaluated the molecular imaging of $^{64}$Cu labeled DOTA-C-ANF$_{4-18}$ (wherein DOTA is 1,4,7,10-tetraazacyclo-dodecane-1,4,7,10-tetracetic acid) for atherosclerotic plaque assessment in a developed animal model with positron emission tomography (PET).

Example 9

This example illustrates the PET tracer production.

We developed a strategy to label DOTA-C-ANF$_{4-18}$ conjugate with $^{64}$Cu for non-invasive imaging of the NPR-C with PET (Scheme 1). The quality control of the labeled peptide was performed with both HPLC and TLC. With C-18 Sep-Pak purification, the radiochemical purity of the $^{64}$Cu-DOTA-C-ANF was higher than 98% confirmed by radio-HPLC. The mass spectrometry of the decayed $^{64}$Cu-DOTA-C-ANF showed one DOTA conjugated to one C-ANF peptide.

Scheme 1: Production of PET tracer for atherosclerotic plaque imaging

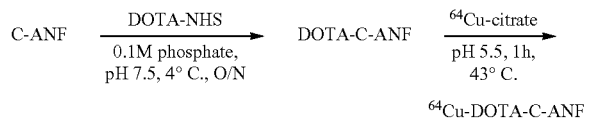

Example 10

We have completed imaging of 11 rabbits (10 injured and 1 control) at various time points, imaging the injured right femoral artery. One rabbit (4831-J) was kept as a control (no special diet and no injury) and another rabbit (1675-K) was used for a blocking study; in which a significant amount of unlabeled natriuretic peptide was injected along with the $^{64}$Cu-labeled natriuretic peptide. Some rabbits were imaged both at 4 and 8 weeks after the second vessel injury (simulating plaque rupture).

TABLE 1

Animal model protocol

| Rabbit | Diet start | 1st Injury | 2nd Injury | Scan 1 | Scan 2 | Scan 3 | Sac Date |
|---|---|---|---|---|---|---|---|
| 1540 (A) | Sep. 1, 2006 | Sep. 14, 2006 | Oct. 16, 2006 | Nov. 7, 2006 | Jan. 19, 2007 | | Jan. 19, 2007 |
| 1621 (B) | Dec. 1, 2006 | Dec. 15, 2006 | N/A | | Feb. 6, 2007 | | Feb. 6, 2007 |
| 1545 (C) | Oct. 10, 2006 | Oct. 25, 2006 | Jan. 18, 2007 | | | Mar. 6, 2007 | Apr. 11, 2007 |
| 1666 (D) | Feb. 12, 2007 | Feb. 27, 2007 | Mar. 26, 2007 | Mar. 20, 2007 | May 1, 2007 | *Jun. 12, 2007* | Jun. 12, 2007 |
| 1673 (E) | Feb. 24, 2007 | Mar. 7, 2007 | Apr. 19, 2007 | Apr. 11, 2007 | May 15, 2007 | | May 15, 2007 |
| 4834 (F) | Jun. 25, 2007 | Jul. 9, 2007 | Aug. 15, 2007 | Aug. 7, 2007 | Sep. 4, 2007 | Oct. 2, 2007 | Oct. 2, 2007 |
| 4835 (G) | Jun. 25, 2007 | Jul. 9, 2007 | Aug. 15, 2007 | Aug. 7, 2007 | Sep. 4, 2007 | Oct. 2, 2007 | Oct. 2, 2007 |
| 4833 (H) | Jul. 9, 2007 | Jul. 23, 2007 | Aug. 28, 2007 | Aug. 21, 2007 | Sep. 18, 2007 | | Sep. 18, 2007 |
| 4842 (I) | Jul. 9, 2007 | Jul. 20, 2007 | Aug. 28, 2007 | Aug. 21, 2007 | Sep. 18, 2007 | Oct. 16, 2007 | Oct. 16, 2007 |
| 4831 (J) | Control | Control | Control | Oct. 16, 2007 | | | Oct. 16, 2007 |
| 1675 (K) | Nov. 15, 2007 | Dec. 10, 2007 | Jan. 7, 2008 | Feb. 5, 2008 | *Feb. 12, 2008* | | Feb. 12, 2008 |

(blank) = No Scan
bold = no PET (tracer failed)
*italics* = no PET (Rabbit died after MR)
*bold, italics* = no MRI (scanner down); special blocking PET study After imaging, rabbits were sacrificed and the femoral arteries removed. Histology stains included H&E, VVG, as well as IHC for the natriuretic peptide receptor. IHC blocking studies were also performed.

Example 11

This example illustrates blood clearance of $^{64}$Cu-DOTA-C-ANF$_{4-18}$.

Figure 7:
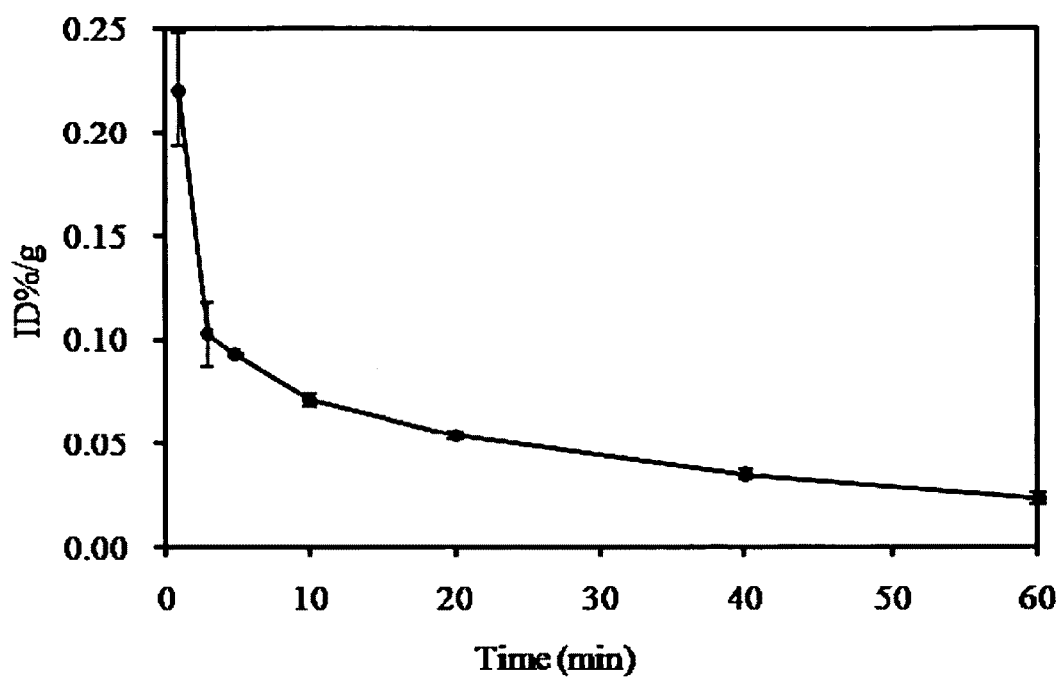
FIG. 7 illustrates activity of $^{64}$Cu-DOTA-C-ANF$_{4-18}$ in blood post injection.

The results from gamma counting showed that at 1 min post injection (p.i.), the activity left in blood was 0.22% ID/g, which decreased sharply to 0.10% ID/g in 2 mins and declined slowly to 0.02% ID/g at 60 min p.i. (FIG. 7). This tracer therefore is a highly sensitive means by which to detect a trace amount of $^{64}$Cu-DOTA-C-ANF in the atherosclerotic animal model Example 12

This example illustrates quantitative PET imaging using a tracer of the present teachings.

Figure 8:
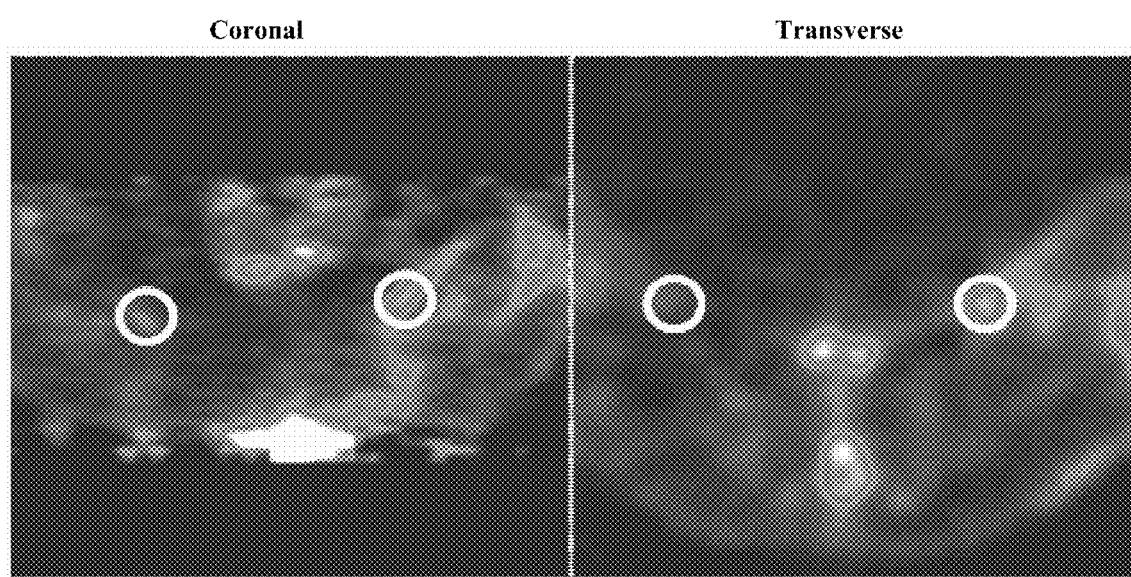
FIG. 8 presents a PET image of $^{64}$Cu-DOTA-C-ANF$_{4-18}$ uptake at an injured artery and at a control site.

In this example, a PET image shows the uptake of $^{64}$Cu-DOTA-C-ANF$_{4-18}$ at the injured artery compared to the control site (FIG. 8). Rabbit #4834 was injected with $^{64}$Cu-DOTA-C-ANF (1 mCi/nmol); images were captured at 0-60 min p.i. dynamic scan.

Figure 9A:
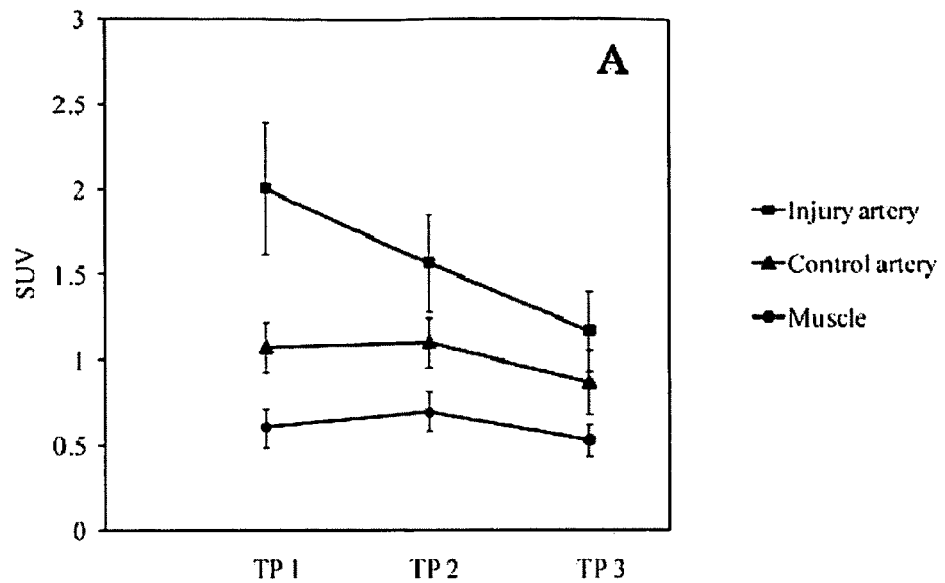
FIG. 9 illustrates a decrease in radiotracer uptake with plaque stabilization.
Figure 9B:
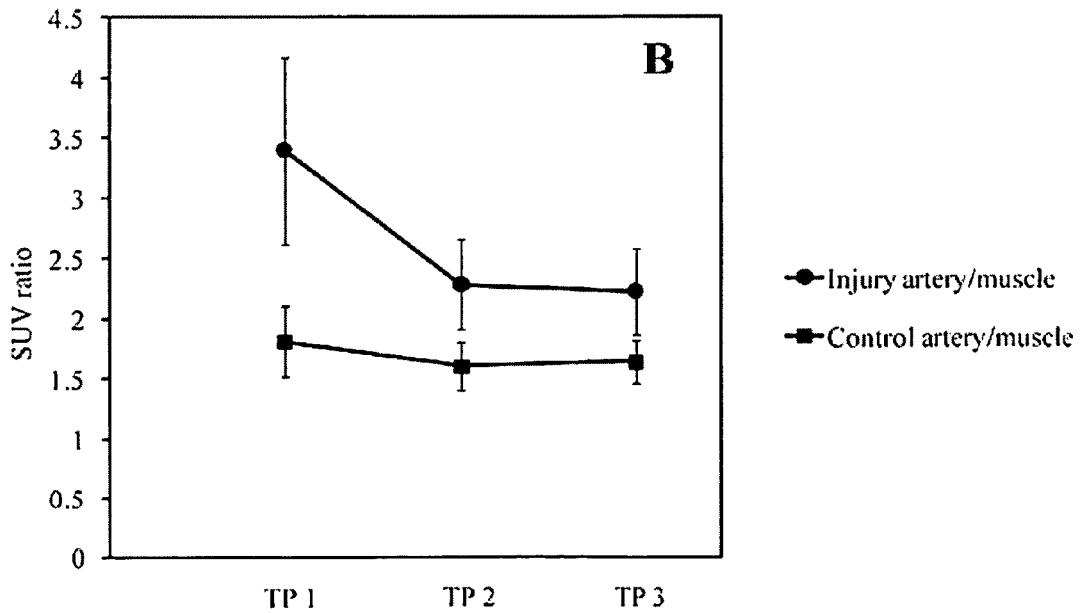

The normalized PET standard uptake values (SUV) (injured site/muscle) shown in FIG. 9 also shows the increase of uptake when the first and second scans are compared, and a decrease in uptake when comparing the second scan to the third. FIG. 9 demonstrates a decrease in radiotracer uptake with plaque stabilization. Panel A shows $^{64}$Cu-DOTA-C-ANF tracer uptake SUV on injured femoral arteries, non-injured control arteries, and surrounding muscle with the progression and remodeling of atherosclerotic plaques. Panel B shows the target-to-background ratios of tracer uptake at the three time points (TP1 (n=8), TP2 (n=6), TP3 (n=4)).

Example 13

This example illustrates specific binding of $^{64}$Cu-DOTA-C-ANF to injured arteries on test animals.

FIG. 10A illustrates a PET image of pre-blocking study, panel B shows a time activity curve of pre-blocking PET image A, panel C shows a PET image of blocking study, and panel D shows the time/activity curve of PET blocking image C.

On representative transverse plane of the MAP reconstructed microPET images the uptake of $^{64}$Cu-DOTA-C-ANF tracer at the injured right femoral artery is evident (A, yellow arrow). The left femoral arteries were used as control and showed weak uptake (A, green arrow). The muscle tracer uptake around the injured artery showed low background (A). On the representative transverse plane of microPET image with C-ANF peptide blocking, both injured artery (yellow arrow) and control artery (green arrow) showed similar weak uptake (C). The time/activity curve (B, D) showed stable uptake in the injured arteries.

The high specific activity of the radiotracer required about 1.1±0.3 μg radiotracer/kg body weight, to produce a target-to-background ratio of 3.39±0.78. Compared to the other published radiotracers on plaque imaging in rabbit model, the SUV uptake of the present teachings is higher than the $^{18}$F-fluorodeoxyglucose, $^{111}$In-low-density-lipoprotein and $^{99m}$Tc-Annexin A5, (Rosen J M, et al. J Nucl Med. 31:343-350, 1990; Ogawa et al. J Nucl Med. 45:1245-1250, 2004; Ishino S, et al. Eur J Nucl Med Mol Imaging. 34:889-899, 2007; Worthley S G, et al. Int J Cardiovasc Imaging. 25:251-257, 2009) comparable to $^{99m}$Tc-Annexin-V, (Kolodgie F D, et al. Circulation. 108:3134-3139, 2003) and lower than $^{125}$I-monocyte chemoattractant peptide 1, $^{99m}$Tc-labeled anti-lect-inlike oxidized low-density lipoprotein receptor-1 antibody. (Ishino S, et al. J Nucl Med. 49:1677-1685, 2008; Ohtsuki K, et al. Circulation. 104:203-208, 2001)

Example 14

This example illustrates blocking studies using PET scanning.

Figure 11:
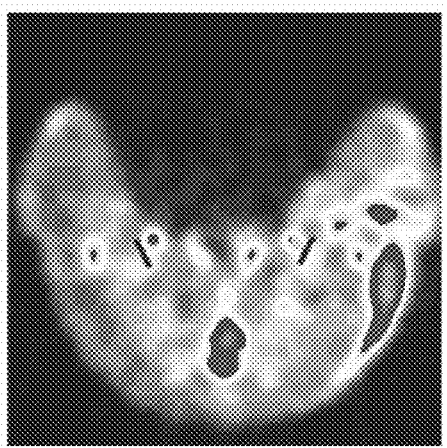
FIG. 11 presents PET images in a blocking study, showing similar uptake of $^{64}$Cu-DOTA-C-ANF$_{4-18}$ at both an injured artery and a control artery.
Figure 11:
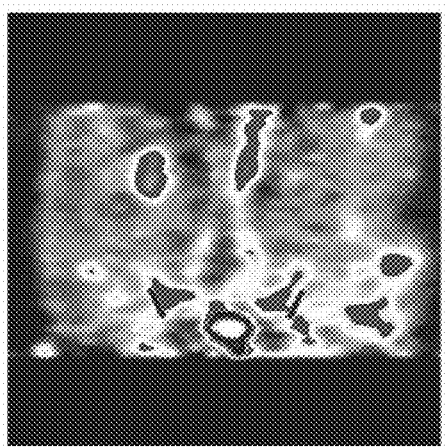

In this example, a PET blocking study was done by co-injecting the PET tracer and C-ANF peptide (2 mg injected) that worked as the blocking agent with 100:1 ratio to the $^{64}$Cu-DOTA-C-ANF$_{4-18}$ (1 mCi/nmol, about 20 micrograms injected). The images (FIG. 11) show similar uptake (n=3) at both the injured artery and control artery (0-60 min p.i. dynamic scan), which was also illustrated in the time activity curve.

The SUV ratio in the blocking studies of injured/control arteries was 1.07±0.06, significantly (P<0.05) lower than that (1.42±0.03) obtained in the pre-blocking studies. The target-to-background ratio on injured artery/muscle was reduced from 3.05±0.19 to 2.13±0.18 due to the competitive receptor blocking (P<0.01). In contrast, the control artery/muscle ratio was hardly altered (2.19±0.16 vs. 2.00±0.06). As a result of receptor blocking, the significant difference (P<0.001) between the injured artery/muscle and control artery/muscle in the pre-blocking studies was changed to no difference in the blocking studies. The average SUVs of injured arteries were declined from 1.69±0.31 to 1.18±0.18 (P<0.05) while the alteration of the control arteries was from 1.21±0.20 to 1.11±0.17 following the blocking studies. The uptake of $^{64}$Cu-DOTA-C-ANF in muscle had an SUV of 0.56±0.11 and 0.55±0.09 before and after the blocking.

Example 15

This example illustrates blocking studies using IHC.

Figure 12:
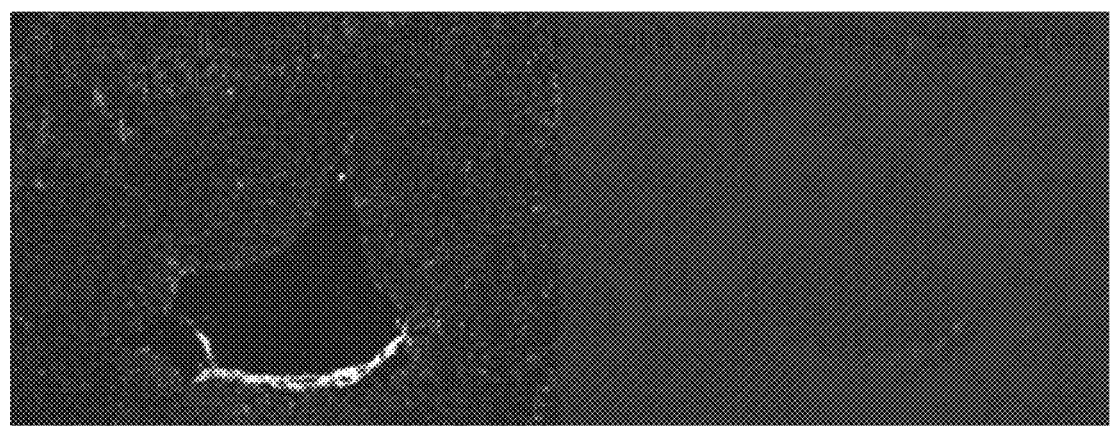
FIG. 12 illustrates an IHC study showing blocking of NPR-C receptor using N-terminus of NPR-C as blocking agent; left panel shows presence of NPR-C receptor, and right panel shows blocking of NPR-C receptor.

In this example, a blocking study was performed using IHC. Peptide blocking of antibody-antigen binding was accomplished by preincubation of appropriately diluted antibody (NPR-C rabbit, Abgent, San Diego, Calif.) with the cognate peptide (0.5 mg/ml) prior to IHC staining. Fluorescence was visualized and recorded with a Zeiss LSM 510 META (Oberkochen, Germany) confocal microscope. The data indicate blocking of NPR-C receptor using N-terminus of NPR-C as blocking agent (FIG. 12).

Example 16

This example illustrates molecular imaging of atherosclerotic lesions using a $^{64}$Cu-labeled NP fragment as a tool for non-invasive plaque imaging with PET.

In this example, C-ANF (atrial natriuretic factor), a C-type NP analog, was functionalized with DOTA and labeled with $^{64}$Cu in 0.1M citrate buffer (pH 5.5). After DTPA challenge and Sep-Pak C-18 purification, the radiochemical purity of $^{64}$Cu-DOTA-ANF was >95%, as measured by radio-HPLC. The right femoral artery of male New Zealand white rabbits fed a cholesterol-rich diet was double-injured by air dessication and balloon overstretching. The presence of atherosclerotic lesion was confirmed by 3T MRI 1 hr after administration of a plaque-targeted contrast agent (Gadofluorine M, Schering AG). A rabbit was injected with $^{64}$Cu-DOTA-ANF (2.8 mCi, ca. 7.5 μg peptide) and a 20 min dynamic scan was acquired on the microPET Focus-220. Fiducial markers attached to the animal bed and filled with a $^{64}$Cu aqueous solution were used to correlate the MRI and microPET images. Histopathologic imaging and IHC of the ex-vivo atherosclerotic artery were performed. IHC demonstrated the presence of NP receptor type-C. MicroPET images clearly showed tracer accumulation at the injury site, with an average SUV of 2.1 during the acquisition scan (3-fold higher than surrounding muscle). In the same time frame, the uninjured control artery was not observable.

All references cited are incorporated by reference each in its entirety.

What is claimed is:

1. A tracer comprising:
    a fragment of a natriuretic peptide which binds C-type natriuretic factor receptor, wherein the fragment is no greater than 25 amino acids in length and comprises the sequence Arg-Ile-Asp-Arg-Ile (SEQ ID NO: 1); and
    a positron-emitting radionuclide.

2. A tracer in accordance with claim 1, wherein the fragment of a natriuretic peptide comprises the sequence Cys-Phe-Gly-Gly-Arg-Ile-Asp-Arg-Ile-Gly-Ala-Cys-NH2, (SEQ ID NO: 2).

3. A tracer in accordance with claim 1, wherein the fragment of a natriuretic peptide comprises a disulfide bond and the sequence H-Arg-Ser-Ser-c[Cys-Phe-Gly-Gly-Arg-Ile-Asp-Arg-Ile-Gly-Ala-Cys]-NH2 (SEQ ID NO: 3).

4. A tracer in accordance with claim 1, wherein the positron-emitting radionuclide is selected from the group consisting of carbon-11, nitrogen-13, oxygen-14, oxygen-15, fluorine-18, iron-52, copper-62, copper-64, zinc-62, zinc-63, gallium-68, arsenic-74, bromine-76, rubidium-82, yttrium-86, zirconium-89, technetium-94m, indium-110m, iodine-122, iodine-123, iodine-124, iodine-131 and cesium-137.

5. A tracer in accordance with claim 4, wherein the positron-emitting radionuclide is selected from the group consisting of carbon-11, nitrogen-13, oxygen-15, fluorine-18, iron-52, copper-64, gallium-68, yttrium-86, bromine-76, zirconium-89, iodine-123, and iodine-124.

6. A tracer in accordance with claim 5, wherein the positron-emitting radionuclide is selected from the group consisting of carbon-11, nitrogen-13, oxygen-15, fluorine-18, and copper-64.

7. A tracer in accordance with claim 6, wherein the positron-emitting radionuclide is a copper-64.

8. A tracer in accordance with claim 7, further comprising a radionuclide carrier moiety.

9. A tracer in accordance with claim 8, wherein the carrier moiety is a dodecanetetraacetic add (DOTA).

10. A method of determining distribution of C-type atrial natriuretic peptide receptors in a subject, comprising:
    administering to the subject a tracer comprising a) a fragment of a natriuretic peptide which binds C-type natriuretic factor receptor, wherein the fragment is no greater than 25 amino acids in length and comprises the sequence Arg-Ile-Asp-Arg-Ile (SEQ ID NO: 1) and b) a positron-emitting radionuclide; and
    subjecting the subject to positron emission tomography scanning.

11. A method in accordance with claim 10, wherein the fragment of a natriuretic peptide comprises the sequence Cys-Phe-Gly-Gly-Arg-Ile-Asp-Arg-Ile-Gly-Ala-Cys-NH2, (SEQ ID NO: 2).

12. A method in accordance with claim 10, wherein the fragment of a natriuretic peptide comprises a disulfide bond and the sequence comprises the sequence H-Arg-Ser-Ser-c[Cys-Phe-Gly-Gly-Arg-fle-Asp-Arg-Ille-Gly-Ala-Cys]-NH2 (SEQ ID NO: 3).

13. A method in accordance with claim 10, wherein the positron-emitting nuclide is selected from the group consisting of carbon-11, nitrogen-13, oxygen-14, oxygen-15 fluorine-18, iron-52, copper-62, copper-64, zinc-62, zinc-63, gallium-68, arsenic-74, bromine-76, rubidium-82, yttrium-86, zirconium-89, technetium-94m, indium-110m, iodine-122, iodine-123, iodine-124, iodine-131 and cesium-137.

14. A method in accordance with claim 13, wherein the positron-emitting radionuclide is selected from the group consisting of carbon-11, nitrogen-13, oxygen-15, fluorine-18, iron-52, copper-64, gallium-68, yttrium-86, bromine-76, zirconium-89, iodine-123, and iodine-124.

15. A method in accordance with claim 14, wherein the positron-emitting radionuclide is selected from the group consisting of carbon-11, nitrogen-13, oxygen-15, fluorine-18, and copper-64.

16. A method in accordance with claim 15, wherein the positron-emitting radionuclide is a copper-64.

17. A tracer comprising:
a fragment of a natriuretic peptide which binds C-type natriuretic factor receptor, wherein the fragment comprises the sequence Arg-He-Asp-Arg-Ile (SEQ ID NO: 1); and
a positron-emitting radionuclide, wherein the tracer does not induce vasodilation in a subject following administration to the subject in an amount effective for imaging atherosclerotic plaque distribution by positron emission tomography (PET) scanning, and wherein the tracer does not contain the entire amino acid sequence of a full-length natriuretic peptide.

* * * * *

UNITED STATES PATENT AND TRADEMARK OFFICE
CERTIFICATE OF CORRECTION

PATENT NO. : 8,436,140 B2
APPLICATION NO. : 12/454810
DATED : May 7, 2013
INVENTOR(S) : P. Woodard et al.

Page 1 of 1

It is certified that error appears in the above-identified patent and that said Letters Patent is hereby corrected as shown below:

In the Claims:

In column 17 line 52, column 17 line 57, column 18 line 66, and column 19 line 5, "-NH2" should be "-NH$_2$" in each occurrence.

In column 19, line 4 should read
[Cys-Phe-Gly-Gly-Arg-Ile-Asp-Arg-Ile-Gly-Ala-Cys]-.

In column 20, line 10 should read
prises the sequence Arg-Ile-Asp-Arg-Ile (SEQ ID NO:.

Signed and Sealed this
Eleventh Day of June, 2013

Teresa Stanek Rea
*Acting Director of the United States Patent and Trademark Office*

SEQUENCE LISTING

<160> NUMBER OF SEQ ID NOS: 3

<210> SEQ ID NO 1
<211> LENGTH: 5

```
<212> TYPE: PRT
<213> ORGANISM: Artificial Sequence
<220> FEATURE:
<223> OTHER INFORMATION: fragment of natriuretic peptide

<400> SEQUENCE: 1

Arg Ile Asp Arg Ile
1               5

<210> SEQ ID NO 2
<211> LENGTH: 12
<212> TYPE: PRT
<213> ORGANISM: Artificial Sequence
<220> FEATURE:
<223> OTHER INFORMATION: fragment of naturiuretic peptide
<220> FEATURE:
<221> NAME/KEY: MOD_RES
<222> LOCATION: (12)..(12)
<223> OTHER INFORMATION: AMIDATION

<400> SEQUENCE: 2

Cys Phe Gly Gly Arg Ile Asp Arg Ile Gly Ala Cys
1               5                   10

<210> SEQ ID NO 3
<211> LENGTH: 15
<212> TYPE: PRT
<213> ORGANISM: Artificial Sequence
<220> FEATURE:
<223> OTHER INFORMATION: fragment of natriuretic peptide
<220> FEATURE:
<221> NAME/KEY: MISC_FEATURE
<222> LOCATION: (4)..(15)
<223> OTHER INFORMATION: circularized
<220> FEATURE:
<221> NAME/KEY: MOD_RES
<222> LOCATION: (15)..(15)
<223> OTHER INFORMATION: AMIDATION

<400> SEQUENCE: 3

Arg Ser Ser Cys Phe Gly Gly Arg Ile Asp Arg Ile Gly Ala Cys
1               5                   10                  15
```